US009040019B2

United States Patent
Siclovan et al.

(10) Patent No.: US 9,040,019 B2
(45) Date of Patent: May 26, 2015

(54) METHODS OF DETECTING MYELIN BASIC PROTEIN

(71) Applicant: General Electric Company, Schenectady, NY (US)

(72) Inventors: Tiberiu Mircea Siclovan, Rexford, NY (US); Cristina Abucay Tan Hehir, Niskayuna, NY (US); Rong Zhang, Niskayuna, NY (US); Victoria Eugenia Cotero, Niskayuna, NY (US); Anshika Bajaj, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 49 days.

(21) Appl. No.: 13/689,819

(22) Filed: Nov. 30, 2012

(65) Prior Publication Data

US 2014/0154178 A1 Jun. 5, 2014

(51) Int. Cl.
*A61K 49/00* (2006.01)
*G01N 33/68* (2006.01)

(52) U.S. Cl.
CPC ........ *A61K 49/0021* (2013.01); *G01N 33/6893* (2013.01); *G01N 2800/285* (2013.01); *A61K 49/0002* (2013.01)

(58) Field of Classification Search
None
See application file for complete search history.

(56) References Cited

U.S. PATENT DOCUMENTS

| 8,169,696 | B2 | 5/2012 | Yazdanfar et al. |
| 2003/0232016 | A1 | 12/2003 | Heinrich |
| 2008/0194970 | A1 | 8/2008 | Steers et al. |
| 2009/0285762 | A1 | 11/2009 | Flower |
| 2010/0222673 | A1 | 9/2010 | Mangat et al. |
| 2011/0286933 | A1 | 11/2011 | Hilderbrand et al. |

FOREIGN PATENT DOCUMENTS

WO 2012031250 A2 3/2012

OTHER PUBLICATIONS

Gibbs-Strauss et al., "Nerve-highlighting Fluorescent Contrast Agents for Image-guided Surgery", Molecular Imaging, vol. 10, Issue 2, pp. 91-101, Apr. 2011.
Whitney et al., "Fluorescent Peptides Highlight Peripheral Nerves during Surgery in Mice", Nature Biotechnology, vol. 29, Issue 4, pp. 352-356, Apr. 2011.
Joseph F. Poduslo et al.; "Macromolecular permeability across the blood-nerve and blood-brain barriers"; Communicated by Ralph T. Holman, Jan. 3, 1994 (received for review Jun. 29, 1993); Proc. Natl. Acad. Sci. USA vol. 91, pp. 5705-5709, Jun. 1994 Neurobiology.
Shigeru Kobayashi et al.; "Imaging of Intraneural Edema by Using Gadolinium-Enhanced MR Imaging: Experimental Compression Injury"; Received Aug. 4, 2004; accepted Nov. 10.; AJNR Am J Neuroradiol 26:973-980, Apr. 2005.
William M. Pardridge et al.; "The Blood-Brain Barrier: Bottleneck in Brain Drug Development"; NeuroRx2. The Journal of the American Society for Experimental NeuroTherapeutics; vol. 2, 3-14, Jan. 2005 © The American Society for Experimental NeuroTherapeutics, Inc.
Mohammad S. Alavijeh et al.; "Drug Metabolism and Pharmacokinetics, the Blood-Brain Barrier, and Central Nervous System Drug Discovery"; vol. 2, 554-571, Oct. 2005 © The American Society for Experimental NeuroTherapeutics, Inc.
Hassan Pajouhesh et al.; "Medicinal Chemical Properties of Successful Central Nervous System Drugs"; Department of Medicinal Chemistry, Neuromed Technologies Inc., Vancouver, British Columbia, Canada V6T 1Z4; and †GRLEN R&D Associates, Andover, Massachusetts 01810-5402; vol. 2, 541-553, Oct. 2005 © The American Society for Experimental NeuroTherapeutics, Inc.

*Primary Examiner* — Michael G Hartley
*Assistant Examiner* — Jennifer Lamberski
(74) *Attorney, Agent, or Firm* — Eileen B. Gallagher

(57) ABSTRACT

A method and a kit for detecting myelin basic protein are provided. The method comprises administering an agent, which binds to myelin basic protein (MBP), to a subject at risk of or diagnosed with a myelin-associated neuropathy, and determining myelination by detecting the agent resided in the subject. The amount of the agent present in the subject is indicative of a myelin-associated neuropathy. A method of quantifying an amount of MBP present in a tissue sample is also provided, wherein the method comprises contacting the tissue sample with the same agent, detecting the agent present in the tissue sample; and quantifying an amount of the agent present in the tissue sample.

23 Claims, 6 Drawing Sheets

METHODS OF DETECTING MYELIN BASIC PROTEIN

STATEMENT REGARDING FEDERALLY SPONSORED RESEARCH & DEVELOPMENT

This invention was made with Government support under contract number R01-EB022872 awarded by the National Institutes of Health through the National Institute of Biomedical Imaging and Bioengineering. The Government has certain rights in the invention.

FIELD

This invention relates to methods of imaging nerves using imaging agents which bind to myelin basic protein (MBP), more particularly to methods of imaging nerves using dyes useful in facile identification of nerves for various applications.

BACKGROUND

Information flow within the nervous system requires the perpetuation of ionic gradients along neurons. Myelin is a lipid-rich dielectric substance that ensheathes axons and provides insulation. The nervous system contains high levels of myelin, which is especially enriched where many myelinated axons are bundled together, collectively called "white matter", as opposed to "grey matter". Because non-nervous system tissues lack myelin, the presence of myelin can distinguish nerve tissue from other tissue types, such as the spinal cord and spinal nerve roots from non-nervous elements of the vertebral column, white matter from grey matter in the brain, and peripheral nerves from muscle tissue. The ability to qualitatively or quantitatively visualize myelin, either in vivo or in vitro, offers researchers and clinicians important diagnostic and treatment tools. For example, the ability to visually identify peripheral nerves during surgery assists surgeons in avoiding cutting or damaging nerves.

Previous efforts in image-guided surgery of nerves utilized modalities that would not require contrast agents or fluorescent labeling of axons by retrograde transport. Challenges in nerve labeling by a retrograde transport approach include the generation of ambiguous signals, the requirement for nerve-stimulation as well as the additional expense of time and effort. In a retrograde transport labeling approach, the labeling efficiency would depend on the exact area of injection and nerves might not be visualized if they fail to take up the contrast agents.

The availability of myelin markers, myelin labeling dyes and myelin-labeling methodologies is paramount in advancing anatomical studies in neuronal research, including neural stem cell research, development of various therapies, and availability of putative animal models of myelin-associated neuropathies. In vivo myelin imaging of the spinal cord assists clinicians in the diagnosis and treatment of spinal cord pathology, such as nerve compression or herniated discs, as well as in diagnosing myelin-associated neuropathies, such as multiple sclerosis and Alzheimer's disease, which stems from damage to myelin within the nervous system. The ability to measure the degree of myelination in vivo in patients with such conditions would aid diagnosing and prognosing myelin-associated neuropathies. Syndromes such as cervical radiculopathy, sciatica, intervertebral disc herniation, and root compression are caused by compression of nerves primarily from tumors or other lesions, which usually results in back or neck pain. The ability to image and identify the source of chronic neck or back pain could enable surgeons to effectively treat these syndromes.

The existing myelin-labeling methodologies include the use of commercially available FluoroMyelin dyes for identification of high myelin content tissues. However, except for a few dyes such as bis-styrene-arylene dyes such as 1,4-bis(p-aminostyryl)-2-methoxy benzene, and (E,E)-1,4-bis(4'-aminostyryl)-2-dimethoxy-benzene, most of the known dyes are unable to cross the blood nerve bather (BNB) or blood brain barrier (BBB).

Myelin is a protein and lipid-rich matrix formed by oligodendrocytes in the central nervous system (CNS) and Schwann cells in the peripheral nervous system (PNS). Because two different cell types in CNS and PNS produce myelin, namely oligodendrocytes and Schwann cells respectively, there are similarities and differences in protein and lipid composition depending on the source of myelin. In both instances, myelin is composed of about 80% lipid fraction and about 20% protein fraction. The lipid fraction in myelin contains cholesterol, cholesterol ester, cerebroside, sulfatide, sphingomyelin, phosphotidylethanolomine, phosphotidylcholine, phosphotidylserine, phosphotidylinositol, triacylglycerol, and diacylglycerol. The protein fraction is composed of several proteins, which include myelin basic protein (MBP), peripheral myelin protein 22 (PMP22), connexin 32 and myelin-associated glycoprotein (MAG), which are produced by both PNS and CNS cells. The myelin protein zero (MPZ) and proteolipid protein produced by the PNS and CNS cells respectively.

The MBP is a major protein component of myelin at 5%-15%, which translates into about 5 mM concentration of MBP. The interaction of MBP with lipids may cause conformational variability and may be critical for exercising its function. An agent that selectively binds to MBP may result in improvements in myelin staining and thereby aid in nerve visualization. Nerve visualization may further be improved through optimal elimination of unbound and nonspecifically bound dye, and improved optical properties allowing for enhanced contrast between myelin and the surrounding tissue. Optical imaging in the near infrared range (NIR), between 700-900 nm, is ideally suited for visualization of myelin in vivo, as the absorption of water, hemoglobin, and lipid are minimal resulting in reduced scatter and improved photon penetration. However, a dye that excites and emits in the visible region is also advantageous. In particular, a specific, targeted fluorophore with a large Stoke shift can provide a high signal-to-background despite operating in the visible region. Furthermore, this approach is complementary to NIR imaging, and does not interfere with NIR fluorescence if multi-channel molecular imaging is desired.

BRIEF DESCRIPTION

Provided herein are methods for the detection and of myelin-associated neuropathy comprising, identifying a subject at risk of or diagnosed with a myelin-associated neuropathy, administering to a subject an agent that binds specifically to MBP, and determining myelination in the subject by detecting the agent.

In one embodiment, a method is provided for detecting myelin-associated neuropathy, comprising administering an agent, that binds specifically to MBP, to a subject at risk of or diagnosed with a myelin-associated neuropathy; determining myelination by detecting the agent resided in the subject; such that the amount of the agent present in the subject is indicative of a myelin-associated neuropathy. The agent comprises a compound of Formula I, a $^{13}$C enriched compound of Formula I, a $^{19}$F-labeled derivative of Formula I, or a radioisotope derivative of Formula I or combinations thereof;

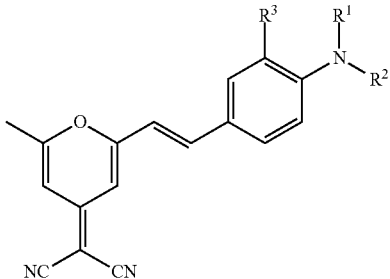
(I)

wherein $R^1$ and $R^2$ are independently at each occurrence a hydrogen, hydroxyl group, $C_1$-$C_{30}$ aliphatic radicals, $C_3$-$C_{30}$ cycloaliphatic radicals, or $C_2$-$C_{30}$ aromatic radicals with the proviso that $R^1$ and $R^2$ are not both equal to a hydroxyl group; $R^3$ is hydrogen, a hydroxyl group, an alkoxy group, a $C_1$-$C_6$ hydroxyalkyl group, a $C_1$-$C_6$ alkyl group or a substituted alkyl group; and the summation of $R^1$, $R^2$ and $R^3$ comprise alkyl groups of less than or equal to 16 carbon atoms.

In another embodiment, a method of imaging nerves in a surgical field is provided, comprising contacting a surgical site of a subject with an agent, and detecting the agent, wherein the agent comprises a compound of Formula I, a $^{13}$C enriched compound of Formula I, an $^{19}$F-labeled derivative of Formula I, a radioisotope derivative of Formula I or combinations thereof;

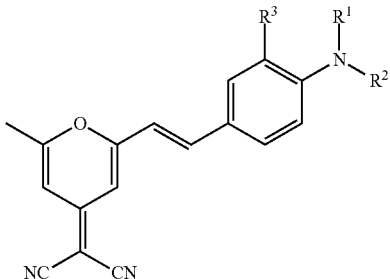
(I)

wherein $R_1$ and $R_2$ are independently at each occurrence a hydrogen, hydroxyl group, $C_1$-$C_{30}$ aliphatic radicals, $C_3$-$C_{30}$ cycloaliphatic radicals, or $C_2$-$C_{30}$ aromatic radicals with the proviso that $R^1$ and $R^2$ are not both equal to a hydroxyl group; $R^3$ is hydrogen, a hydroxyl group, an alkoxy group, a $C_1$-$C_6$ hydroxyalkyl group, a C1-C6 alkyl group or a substituted alkyl group; and the summation of $R^1$, $R^2$ and $R^3$ comprise alkyl groups of less than or equal to 16 carbon atoms.

In yet another embodiment, a method of quantifying an amount of MBP present in a tissue sample is provided, comprising contacting the tissue sample with an agent; and quantifying an amount of the agent present in the tissue sample. The agent comprises a compound of Formula I, a $^{13}$C enriched compound of Formula I, an $^{19}$F-labeled derivative of Formula I, a radioisotope derivative of Formula I or combinations thereof;

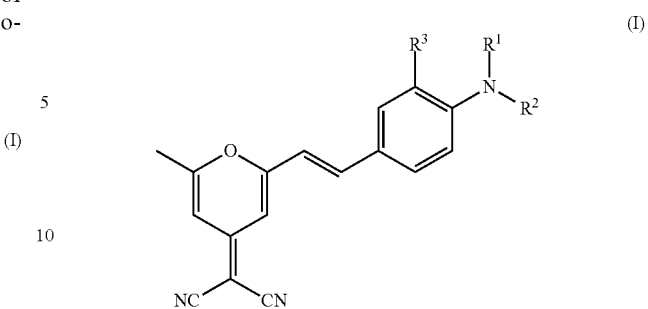
(I)

wherein $R^1$ and $R^2$ are independently at each occurrence a hydrogen, hydroxyl group, $C_1$-$C_{30}$ aliphatic radicals, $C_3$-$C_{30}$ cycloaliphatic radicals, or $C_2$-$C_{30}$ aromatic radicals with the proviso that $R^1$ and $R^2$ are not both equal to a hydroxyl group; $R^3$ is hydrogen, a hydroxyl group, an alkoxy group, a $C_1$-$C_6$ hydroxyalkyl group, a $C_1$-$C_6$ alkyl group or a substituted alkyl group; and the summation of $R^1$, $R^2$ and $R^3$ comprise alkyl groups of less than or equal to 16 carbon atoms.

In some embodiments, a kit for detecting myelin-associated neuropathy in a subject is provided and comprises an agent and a pharmaceutically acceptable carrier, wherein the agent comprises a compound of Formula I, a $^{13}$C enriched compound of Formula I, an $^{19}$F-labeled derivative of Formula I, or a radioisotope derivative of Formula I;

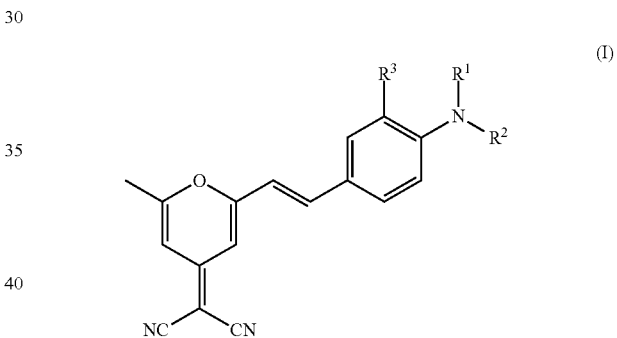
(I)

wherein $R^1$ and $R^2$ are independently at each occurrence a hydrogen, hydroxyl group, $C_1$-$C_{30}$ aliphatic radicals, $C_3$-$C_{30}$ cycloaliphatic radicals, or $C_2$-$C_{30}$ aromatic radicals with the proviso that $R^1$ and $R^2$ are not both equal to a hydroxyl group; $R^3$ is hydrogen, a hydroxyl group, an alkoxy group, a $C_1$-$C_6$ hydroxyalkyl group, a $C_1$-$C_6$ alkyl group or a substituted alkyl group; and the summation of $R^1$, $R^2$ and $R^3$ comprise alkyl groups of less than or equal to 16 carbon atoms.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
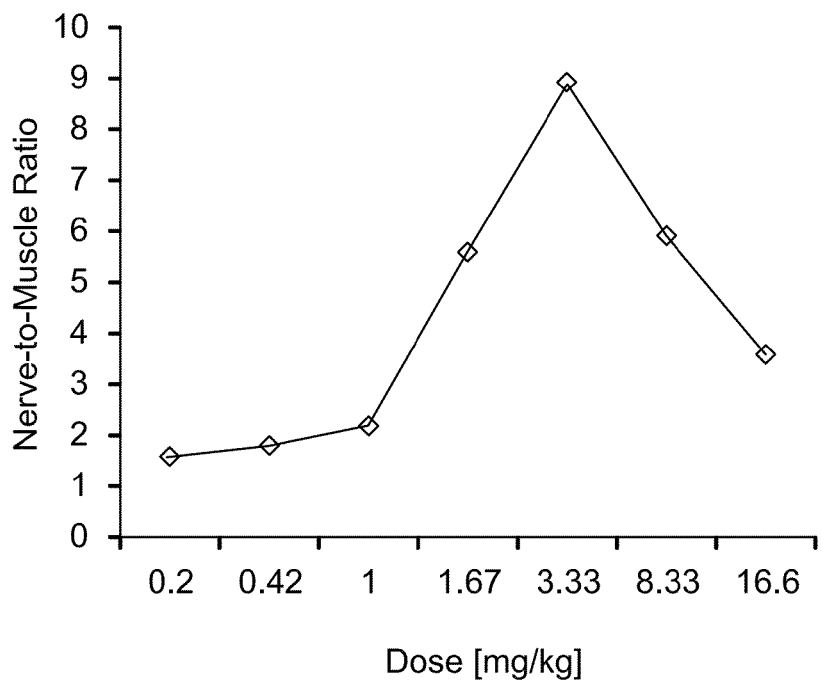
FIG. 1 is a graph showing a dose-response pattern of a compound of Formula II in adult male CD-1 mice following intra venous (IV) injection of the compound.

In the following specification and the claims, which follow, reference will be made to a number of terms, which shall be defined to have the following meanings.

The singular forms "a", "an" and "the" include plural referents unless the context clearly dictates otherwise.

As used herein, the term "myelin-associated neuropathy" generally refers to any condition in which the insulating material ensheathing portions of neuronal cells becomes damaged or dysfunctional as a component of a syndrome, disease, or other pathological condition, such as, but not limited to, multiple sclerosis, traumatic brain injury, stroke, Guillain-Barré syndrome, Alzheimer's disease, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy induced neuropathy, or any combination thereof. The term may also refer to neuropathy associated with surgical damage.

As used herein, the term "agent" refers to a compound to be administered at a desired concentration and efficacy for nerve binding or labeling. The agent may be suspended or dissolved in solvents, stabilization aids, buffers or fillers.

A compound exhibits "specific binding" for myelin if it associates more frequently with, more rapidly with, for a longer duration with, or with greater affinity to, myelin than with tissues not containing myelin. "Non-specific binding" refers to binding of the agent to non-myelin containing tissue. For relative binding values, such as specific binding or non-specific binding, each sample should be measured under similar physical conditions (i.e., temperature, pH, formulation, and mode of administration). Generally, specific binding is characterized by a relatively high affinity of an agent to a target and a relatively low to moderate capacity. Typically, binding is considered specific when the dissociation constant, $K_d$, is below $10^{-4}$ M. A lower $K_d$ indicates greater affinity, and thus typically greater specificity. For example, antibodies typically bind antigens with an affinity constant in the range of $10^{-6}$ to $10^{-9}$ M or lower. "Non-specific" binding usually has a low affinity with a moderate to high capacity. Non-specific binding usually occurs when the affinity constant is above $10^{-4}$ M. Controlling the time and method used to contact the agent with the tissues reduces non-specific binding.

As used herein, the term "baseline fluorescence" refers to the frequency and magnitude of electromagnetic radiation emitted by a tissue or sample of tissue upon being exposed to an external source of electromagnetic radiation in the absence of administration or binding of any fluorescing compound, as distinguished from the radiation emitted following the administration and binding of such fluorescing compound and exposure to an external source of electromagnetic radiation.

As used herein, the term "control" or "control sample" refers to a tissue sample of a similar size, morphology, or structure as the tissue sample to be analyzed, and with a level of myelin whereby the sample's level of myelin serves as a reference to which other samples' myelin levels may be compared. The control sample usually devoid of administered agent or compound for nerve labeling.

As used herein, the term "parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, intraspinal injection, intrathecal injection, intracerebral injection, intracerebroventricular injection, or intraspinal injection or any combination thereof.

As used herein, the term "formulation buffer" refers to a composition which allows the application of the agent material to the site of the application, surrounding tissues, or prepared tissue section to allow the agent to have an effective residence time for specific binding to the target or to provide a convenient manner of release. Solubilization strategies may include but are not limited to: pH adjustments, salt formation, formation of ionizable compounds, use of co-solvents, complexation, surfactants and micelles, emulsions and microemulsions. The formulation buffer may include, but is not limited to, a solubilizer, detergent, buffer solution, stabilizers, and preservatives. Examples of these include but are not limited to, HCl, citric acid, DMSO, propylene glycol, ethanol PEG 300, cyclodextrans, citrate, acetate, phosphate, carbonate or tris(hydroxymethyl)aminomethane.

As used herein, the term "demyelination model" refers to any experimentally-induced damage to, or dysfunction of, the insulating material ensheathing portions of neuronal cells, that may be utilized in the experimental study of neuropathic demyelination, including, but not limited to, experimental allergic encephalomyelitis.

As used herein, the term "re-myelination" refers to the spontaneous, therapeutic, or experimentally induced repair, regeneration, or otherwise enhanced constitution or functionality of the insulating material ensheathing neuronal axons.

Unless otherwise indicated, all numbers expressing quantities of ingredients, properties such as molecular weight, reaction conditions, and so forth used in the specification and claims are to be understood as being modified in all instances by the term "about." In some instances, the approximating language may correspond to the precision of an instrument for measuring the value. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Many of the compounds described herein may comprise one or more asymmetric centers and may thus give rise to enantiomers, diastereomers, and other stereoisomeric forms that may be defined, in terms of absolute stereochemistry, as (R)- or (S)-. The chemical structure of the agent includes for example, without limitation, all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also included.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having $4n+2$ "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical comprised of a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO-), 3-methylphen-1-yl, methylenebis(4-phen-1-yloxy) (i.e., —OPhCH$_2$PhO-), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO-), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphen-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term, "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}$(CF$_3$)$_2$ $C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy(2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical. In certain embodiments the aliphatic radical may also comprise an hydroxyl-terminated polyethyleneglycol Many of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

"Alkyl" is intended to include linear, branched, or cyclic hydrocarbon structures and combinations thereof, including lower alkyl and higher alkyl. Alkyl groups are those of C20 or below. "Lower alkyl" refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

As used herein, the term "substituted" refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, OCH $(COOH)_2$, cyano, primary amino, secondary amino, acylamino, alkylthio, sulfoxide, sulfone, phenyl, benzyl, phenoxy, benzyloxy, heteroaryl, or heteroaryloxy.

As used herein, the term "electron donating group" refers to chemical groups that add electron density to the conjugated π system making it more nucleophilic. Electron donating groups may be recognized by lone pairs of electrons on an atom adjacent to the π system. Examples of electron donating groups include, but are not limited to, —NR'R", —NHR, —$NH_2$, —OH, —OR, —NHCOR, —OCOR, —R, —$C_6H_5$, and —CH=$CR_2$.

One or more embodiments of a method of detecting myelin-associated neuropathy are provided. The method comprises administering an agent to a subject at risk of or diagnosed with a myelin-associated neuropathy, determining myelination by detecting the agent resided in the subject, and comparing the myelination in the subject with a control sample administered with the same agent, wherein an amount of the agent present in the subject is indicative of a myelin-associated neuropathy, and wherein the agent comprises a compound of Formula I, a $^{13}C$ enriched compound of Formula I, a $^{19}F$-labeled derivative of Formula I, or a radioisotope derivative of Formula I or combinations thereof;

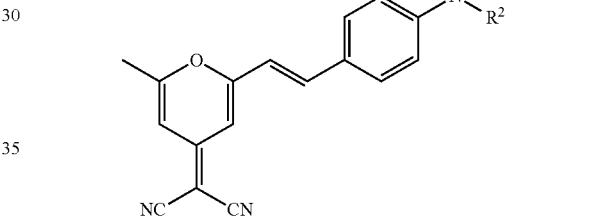

(I)

wherein $R^1$ and $R^2$ are independently at each occurrence a hydrogen, hydroxyl group, $C_1$-$C_{30}$ aliphatic radicals, $C_3$-$C_{30}$ cycloaliphatic radicals, or $C_2$-$C_{30}$ aromatic radicals with the proviso that $R^1$ and $R^2$ are not both equal to a hydroxyl group; $R^3$ is hydrogen, a hydroxyl group, an alkoxy group, a $C_1$-$C_6$ hydroxyalkyl group, a $C_1$-$C_6$ alkyl group or a substituted alkyl group; and the summation of $R^1$, $R^2$ and $R^3$ comprise alkyl groups of less than or equal to 16 carbon atoms.

In some embodiments, the methods are used for the qualitative or quantitative detection of MBP in an in vitro or in vivo sample utilizing specific binding of an agent to MBP. The specific binding to MBP may be by an agent comprising the compound of Formula I, a $^{13}C$ enriched compound of Formula I, a $^{19}F$-labeled-derivative of Formula I, or a radioisotope derivative of Formula I.

As noted, $R^1$ and $R^2$ are independently at each occurrence a hydrogen, or a group consisting of $C_1$-$C_{30}$ aliphatic radicals, $C_3$-$C_{30}$ cycloaliphatic radicals, $C_2$-$C_{30}$ aromatic radicals. In some embodiments, at least one of the $R^1$ and $R^2$ is hydrogen, an alkyl, a hydroxyalkyl, or an aminobenzyl group. In some embodiments, $R^1$ is the same as $R^2$. Accordingly, in one example, if the $R^1$ is an alkyl group, such as an ethyl group, then $R^2$ is also an ethyl group and vice versa. In some other examples, if the $R^1$ is a hydroxyalkyl group, such as hydroxyethyl group, then $R^2$ is also a hydroxyethyl group and vice versa. In one specific embodiment, $R^1$ and $R^2$ are both hydrogen. In some embodiments, either of the $R^1$ and $R^2$ is a hydroxyl group. In these embodiments, if $R^1$ is a hydroxyl group, $R^2$ is a hydrogen, alkyl, or hydroxyalkyl group, as a compound of Formula VI-A. For example, if $R^1$ is hydroxyl, $R^2$ is an ethyl group.

As noted, $R^3$ is hydrogen, a hydroxyl group, an alkoxy group, a $C_1$-$C_3$ hydroxyalkyl group, a $C_1$-$C_3$ alkyl group or a substituted alkyl group. In some embodiments, $R^3$ is a lower alkyl group of from 1 to 6 carbon atoms, or an alkoxy group. Accordingly, in some embodiments, $R^3$ is a hydroxyl group. In some other embodiments, $R^3$ is a $C_1$-$C_3$ hydroxyalkyl group, for example a hydroxymethyl, hydroxyethyl, hydroxypropyl or hydroxybutyl group.

As noted, the compound of Formula I is used as a nerve labeling dye, with the proviso that a summation of $R^1$, $R^2$ and $R^3$ is less than or equal to 16 C atoms. In some embodiments, the total length of the claimed $R^1$, $R^2$, and $R^3$ is less than 16 methylene units. In some embodiments, the total length of the claimed R', $R^2$, and $R^3$ is equal to 16 methylene units. In one or more examples of a compound, $R^1$ is methyl (C1), $R^2$ is butyl (C4) and $R^3$ is undecyl (C11). In some embodiments of a compound, $R^1$ is ethyl (C2), $R^2$ is butyl (C4) and $R^3$ is decyl (C10). In some other embodiments of a compound, $R^1$ is butyl (C4), $R^2$ is propyl (C3) and $R^3$ is nonyl (C9) or any such combinations.

In some embodiments, $R^1$ and $R^2$ are a lower alkyl group of from 1 to 6 carbon atoms, and include methyl, ethyl, n-propyl, isopropyl, and n-, s- and t-butyl. In some embodiments, $R^1$ and $R^2$ are electron donating groups. The electron donating group may include a primary, secondary, or tertiary amine (—$NH_2$, —NHR, —NR'R"), or an alkoxy group (—OR).

The agents for labeling the nerves comprise the compounds, wherein the compounds may be designed to meet the requirements for crossing the blood-brain bather (BBB), the blood-nerve bather (BNB), or both. In one or more embodiments, the compound is designed to cross the BBB. In one or more embodiments, the compound is designed to cross the BNB. As noted, the compounds are designed to cross the BBB or BNB, the term "designed" refers to constructing the compounds such that summation of the functional moieties of the compounds define the physical or chemical properties of the compounds. For example, various substituents may be selected based on overall molecular weight, partition coefficient or H-bonding of the compound. The conditions for crossing the BBB or BNB may include but are not limited to molecular weight, partition coefficient (Log P), number of H-bonding interactions or surface-charge of the molecules. In certain embodiments, the molecules which crosses BBB or BNB, may be desirable to have a Log P value of less than or equal to 5, number of H-bond donors ≤3, number of H-bond acceptors ≤7, polar surface area ≤90 sq Angstrom and a molecular weight ≤500 Da.

In one or more embodiments, a molecular weight of the agent for nerve labeling dye is less than or equal to 500 Da. In one example, the compound has a formula (I), wherein the sum of $R^1$, $R^2$, and $R^3$ substitutions is equal to 16 methylene units.

In one or more embodiments, the Log P value of the compound is less than or equal to 5. In some embodiments, a compound with at least two R groups, such as $R^1$ and $R^2$, comprising more than 4 C atoms, may exceed the Log P value of 5 and that may increase the lipophilicity. In some embodiments, the compound of the present invention comprises alkoxy or poly(alkoxy) groups, for example in certain embodiments, the poly(alkoxy) group may comprise polyethoxy groups. The alkoxy or polyalkoxy groups may reduce the value of Log P closer to the desired value of 1-5. Typically, the terminal OH group is a H-bonding donor, each ethoxy counts as a H-bonding acceptor. In some embodiments, $R^1$, $R^2$ are ($CH_2CH_2O$)n-H, with n=1-5 while $R^3$ is —O($CH_2$)n-H or —($OCH_2CH_2$)n-OH. In some other embodiments, either of the $R^1$ and $R^2$ is hydroxyl or protected hydroxyl, such as $R^1$ is hydroxyl, and $R^2$ is hydrogen, alkyl, alkoxy or hydroxyalkyl.

In some embodiments of the method, the Log P value of the compound is less than or equal to 5. Typically, the increase in Log P value increases the lipophilicity of the compounds. The use of excessively lipophilic compounds in innervated areas surrounded by adipose tissue may lead to excessive agent accumulation in the adipose tissue and may result in difficult differentiation between nerve and surrounding tissue.

In one embodiment, the nerve labeling agent comprises a compound of Formula (II)

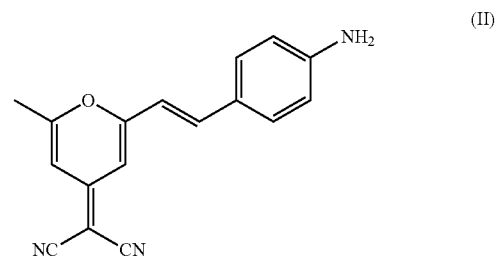 [SMILES: CC1=CC(=C(C#N)C#N)C=C(/C=C/c2ccc(N)cc2)O1]

In one embodiment, the nerve labeling agent comprises a compound of Formula (III)

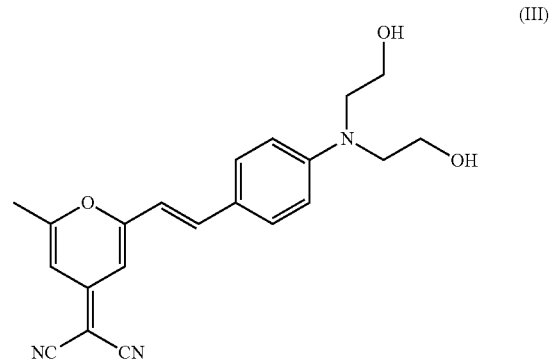 [SMILES: CC1=CC(=C(C#N)C#N)C=C(/C=C/c2ccc(N(CCO)CCO)cc2)O1]

In one embodiment, the nerve labeling agent comprises a compound of Formula (IV)

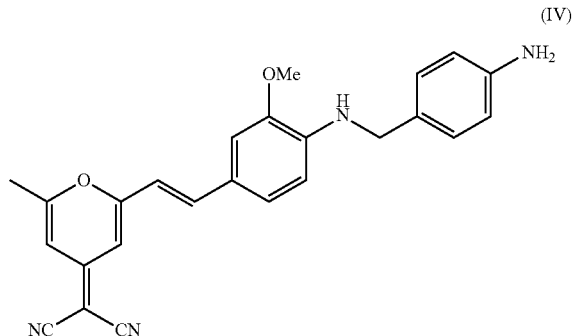 [SMILES: COc1cc(/C=C/C2=CC(=C(C#N)C#N)C=C(C)O2)ccc1NCc1ccc(N)cc1]

In one embodiment, the nerve labeling agent comprises a compound of Formula (V)

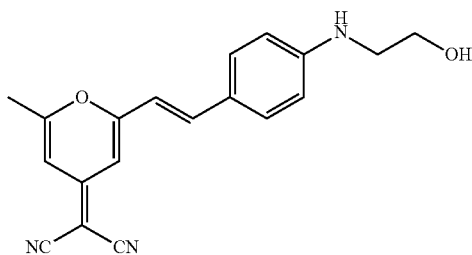

(V)

In one embodiment, the nerve labeling agent comprises a compound of Formula (VI)

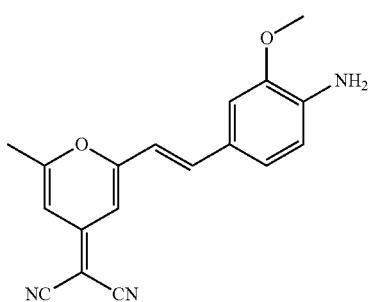

(VI)

In one embodiment, the nerve labeling agent comprises a compound of Formula (VII)

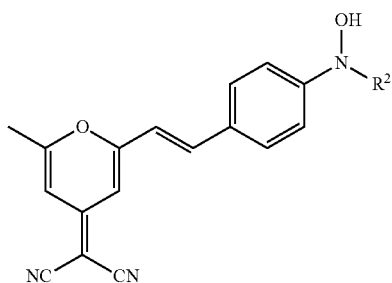

(VII)

wherein $R^2$ is a hydrogen, alkyl, or hydroxyalkyl group.

In one embodiment, the nerve labeling agent comprises a compound of Formula (VIII).

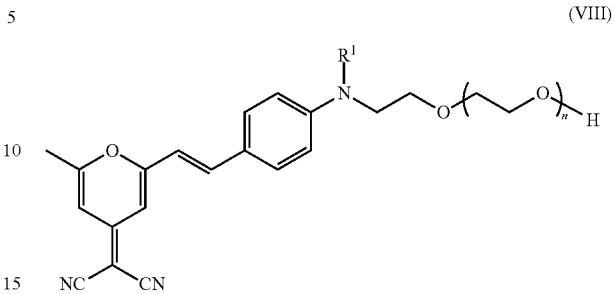

(VIII)

wherein $R^1$ is a hydrogen, a hydroxyl group, alkyl, hydroxyalkyl, and n is an integer between 0 and 4.

In one embodiment, the nerve labeling agent comprises a compound of Formula (IX)

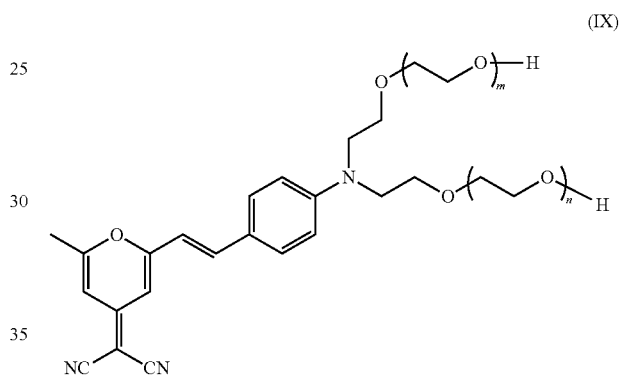

(IX)

wherein m and n are integers, m+n is less than or equal to 4.

In some embodiments, agents having a structure similar to that of Formula I were synthesized and subjected to the nerve binding assay and the fluorescence assay. In certain instances wherein the agents were structurally similar to the compounds of Formula II to IX, but have a pendent five member ring, the agents lacked noticeable binding to nerves. It should be noted that the agents were fluorescent. These agents are illustrated in Table 1 below.

TABLE 1

Examples of fluorescent compounds lacking nerve binding property and the optical properties of the compounds in DMSO.

| Compound | Structure | Abs[#] | Em[#] |
|---|---|---|---|
| A | 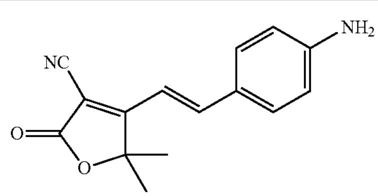 [SMILES: CC1(C)OC(=O)C(C#N)=C1/C=C/c1ccc(N)cc1] | 480 | 562 |

TABLE 1-continued

Examples of fluorescent compounds lacking nerve binding property and the optical properties of the compounds in DMSO.

| Compound | Structure | Abs[#] | Em[#] |
|---|---|---|---|
| B | 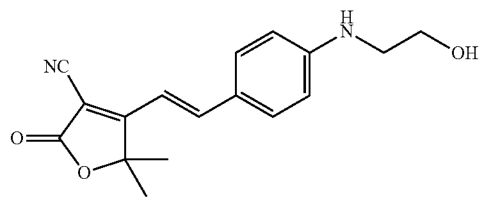 [SMILES: CC1(C)OC(=O)C(C#N)=C1/C=C/c1ccc(NCCO)cc1] | 494 | 578 |
| C | 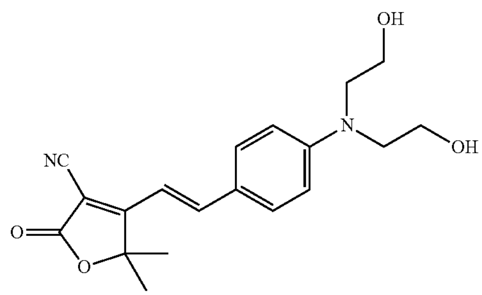 [SMILES: CC1(C)OC(=O)C(C#N)=C1/C=C/c1ccc(N(CCO)CCO)cc1] | 505 | 591 |
| D | 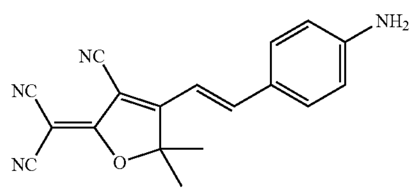 [SMILES: CC1(C)OC(=C(C#N)C#N)C(C#N)=C1/C=C/c1ccc(N)cc1] | 574 | 621 |
| E | 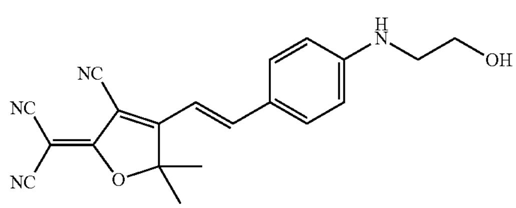 [SMILES: CC1(C)OC(=C(C#N)C#N)C(C#N)=C1/C=C/c1ccc(NCCO)cc1] | 590 | 636 |
| F | 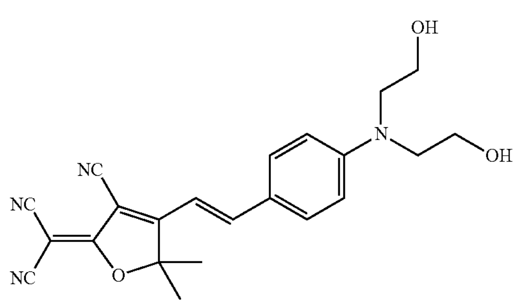 [SMILES: CC1(C)OC(=C(C#N)C#N)C(C#N)=C1/C=C/c1ccc(N(CCO)CCO)cc1] | 596 | 656 |

[#]Absorption (Abs) and Emission (Em) are the maximal absorbance and fluorescence emission wavelength in nanometers (nm).

In other instances, agents having a structure similar to that of Formula II to IX were synthesized but either lacked fluorescence properties or had reduced fluorescence emission properties. As such, nerve binding for these agents would be difficult to assess. Examples of these agents are further illustrated in Table 2 below.

TABLE 2

Examples of agents without or with reduced fluorescent properties

| Entry (compound) | Structure |
| --- | --- |
| G | 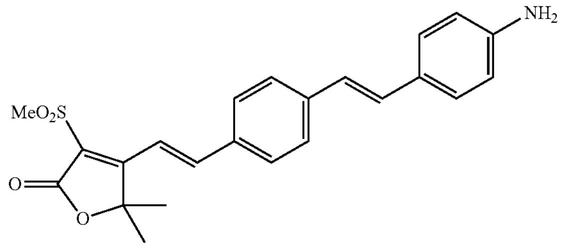 [SMILES: CC1(C)OC(=O)C(S(C)(=O)=O)=C1/C=C/c1ccc(/C=C/c2ccc(N)cc2)cc1] |
| H | 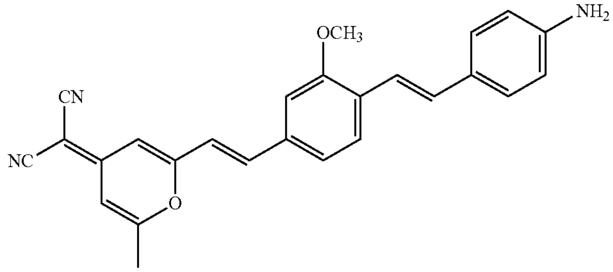 [SMILES: COc1cc(/C=C/C2=CC(=C(C#N)C#N)C=C(C)O2)ccc1/C=C/c1ccc(N)cc1] |
| I | 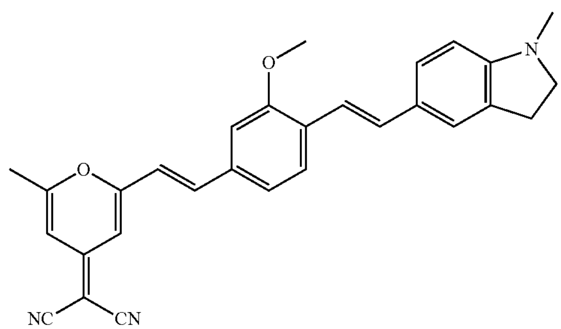 [SMILES: COc1cc(/C=C/C2=CC(=C(C#N)C#N)C=C(C)O2)ccc1/C=C/c1ccc2c(c1)CCN2C] |
| J | 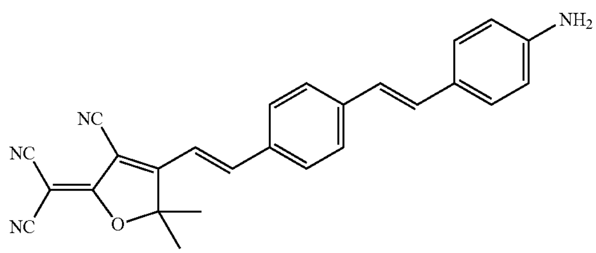 [SMILES: CC1(C)OC(=C(C#N)C#N)C(C#N)=C1/C=C/c1ccc(/C=C/c2ccc(N)cc2)cc1] |

In certain embodiments, the agents may be used to image nerves. In one embodiment, a method of imaging nerves in a surgical field comprises contacting a surgical site of a subject with an agent, and detecting the agent, wherein the agent comprises a compound of Formula I, a $^{13}C$ enriched compound of Formula I, an $^{19}F$-labeled derivative of Formula I, a radioisotope derivative of Formula I or combinations thereof.

As noted, after administration of the agent, the method further comprises determining myelination by detecting the agent residing in the subject. In some embodiments, the agent binds to nerve tissue at the surgical site. In some other embodiments, the agent binds to the myelin of the nerve tissue at the surgical site. In one or more embodiments, the agent binds to MBP of the nerve tissue at the surgical site. The methods for the qualitative or quantitative detection of MBP in an in vitro or in vivo sample may utilize specific binding of the agent administered to the MBP.

Figure 2:
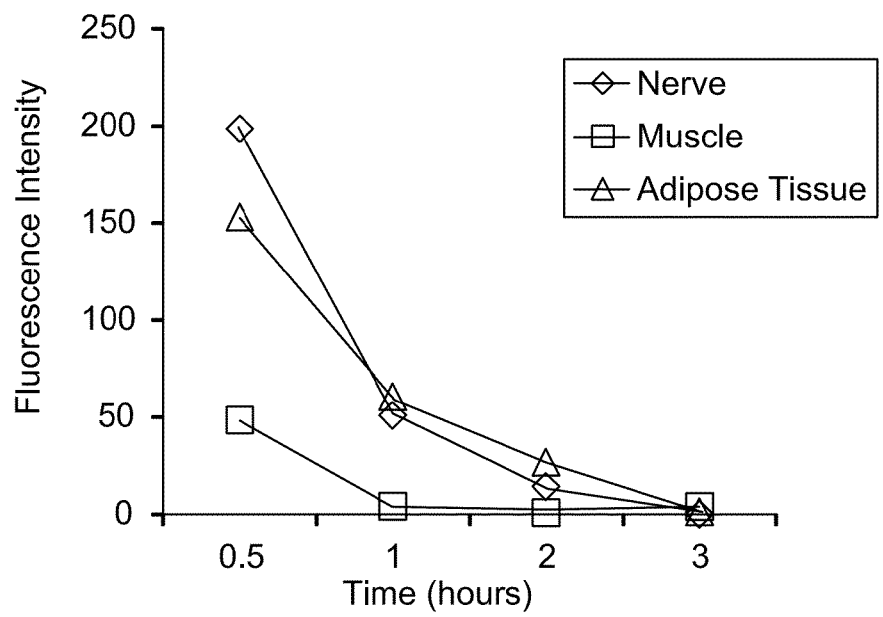
FIG. 2 is a graph showing the kinetics of clearance of a compound having Formula II following IV injection in adult male CD-1 mice, wherein the maximum tissue-specific fluorescence intensity decreases with increasing time post injection, for nerve, muscle, and adipose tissue.
Figure 3A:
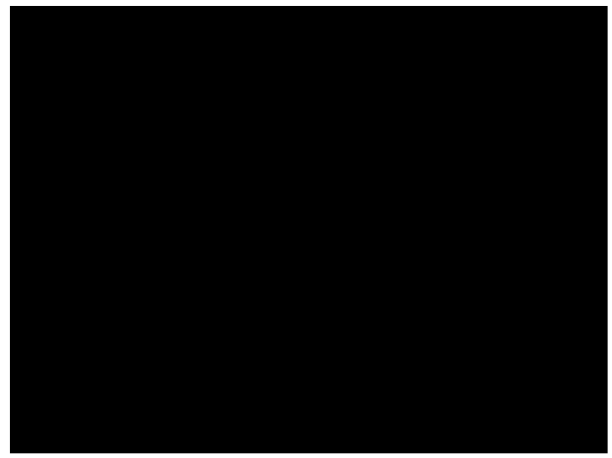
FIGS. 3A, 3B and 3C are images result from fluorescence in vivo imaging of the nerves of a Sprague-Dawley (SD) rat, following IV injection of buffer without any agent (control), with 16.67 mg/kg of compound having Formula II and with 8.33 mg/kg of compound having Formula II, respectively.
Figure 3B:
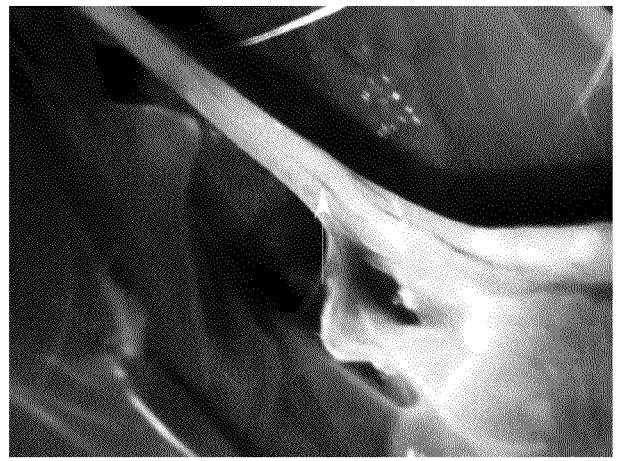
Figure 3C:
Figure 4A:
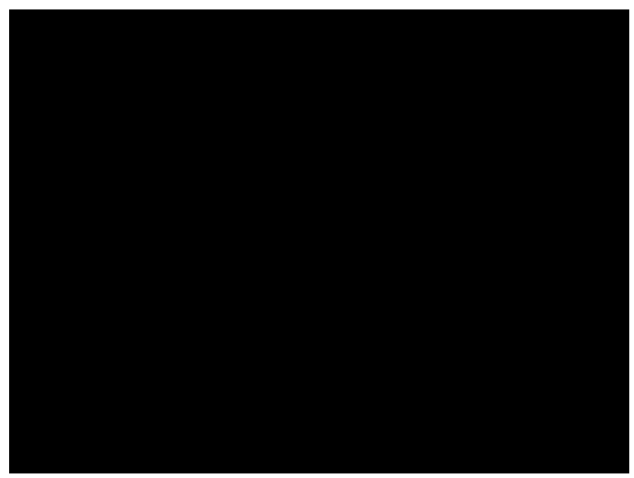
FIGS. 4A, 4B and 4C show the overall effect of formulation on nerve and adjacent tissue fluorescence in SD rats, treated with a single IV injection with 8.33 mg/kg of a compound having Formula II formulated in a buffer containing 10% 2-Hydroxypropyl-β-Cyclodextrin (2-HPβCD), 15% 2-HPβCD or 25% 2-HPβCD respectively at 0.5 hour post-injection.
Figure 4B:
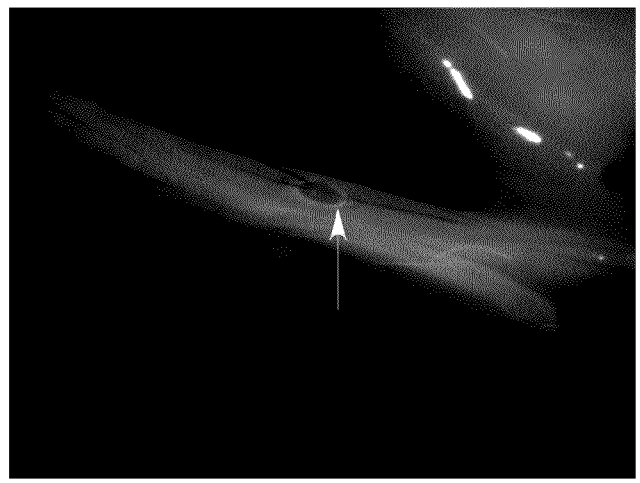
Figure 4C:

In one or more embodiments, the agent-associated with the nerve tissue may be easily distinguished from the surrounding adipose tissue or muscle, as the agents bound to nerve tissue are optically detectable at specific wavelengths. In one or more embodiments, the nerve-to-muscle ratio increases and reaches maximum at the dose of about 3.3 mg/kg of the agent, as shown in FIG. 1. The nerve-to-muscle ratio was calculated using the total fluorescence in the nerve as compared to that of adjacent muscle tissue. In general, a nerve-to-muscle ratio above 1.5 provides visually acceptable contrast of target compared to non-target tissue in fluorescence imaging, with higher ratio giving better quality images. In some embodiments, the optimized dose of 3.3 mg/kg of the agent is used for determining binding of the agents to nerves. The agents (dyes) fluoresce red when illuminated with a light in a blue region of the visible spectrum, thus highlighting the myelinated nerves. FIG. 2 shows the maximum signal intensity in a highlighted nerve as well as adjacent muscle and adipose tissue. A moderate increase in fluorescence intensity is notable in the nerve upon agent-binding as compared to the same in adjacent adipose tissue. The agents exhibit non-specific partitioning to adipose tissue as a result of their lipophilicity, a requirement for BBB and BNB penetration. Upon binding of the agents, the nerve fluorescence intensity is significantly greater than that of adjacent muscle, as shown in FIGS. 3B-3C and FIGS. 4B-4C wherein FIG. 3A and FIG. 4A are control (without administering the agent).

Figure 5C:
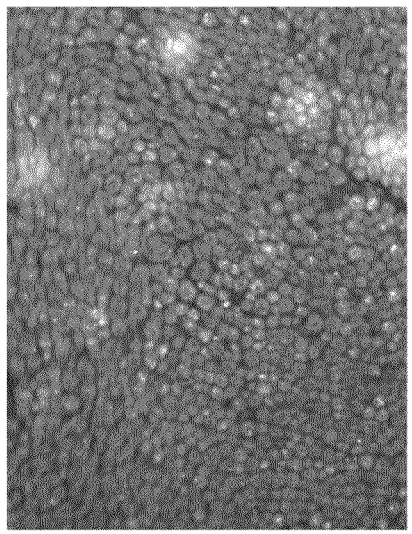
FIGS. 5A, 5B, 5C, 5D and 5E are fluorescence microscope images showing ex vivo binding of the different nerve labelling agents to sciatic nerve tissue sections compared to a control FIG. 5F, used to measure autofluorescence.
Figure 5F:
Figure 5B:
Figure 5E:
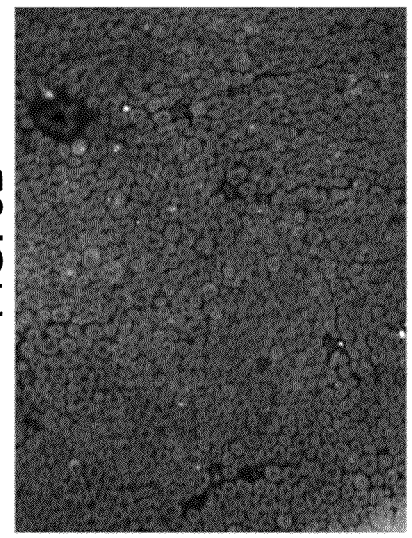
Figure 5A:
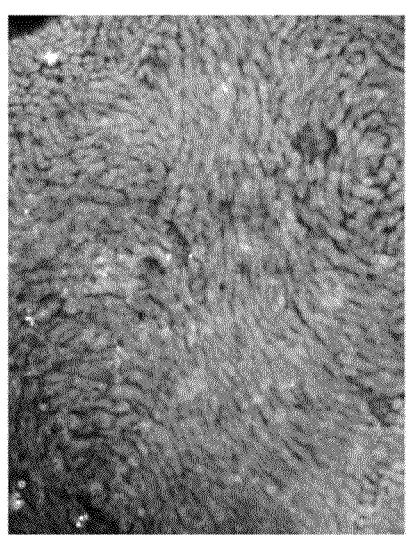
Figure 5D:
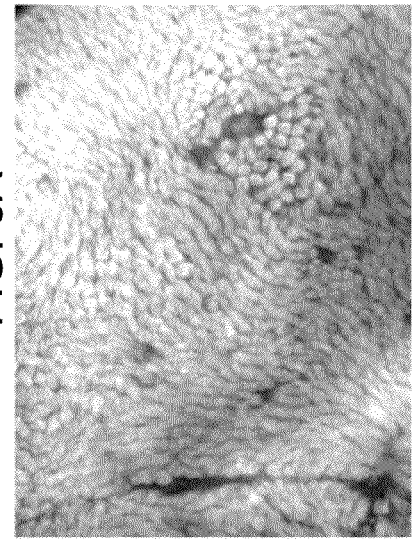

The images for ex vivo binding of various agents (compounds) to sciatic nerve tissue sections under a fluorescence microscope are shown in FIGS. 5 A to FIG. 5E compared to control FIG. 5F (without administering any agent). As shown in FIGS. 5A, 5B, 5C, 5D and 5E, fluorescence signal is evident in the presence of the nerve labeling agents, such as compounds having Formula II, III, IV, V and VI respectively, but not in the control tissue.

Figure 6A:
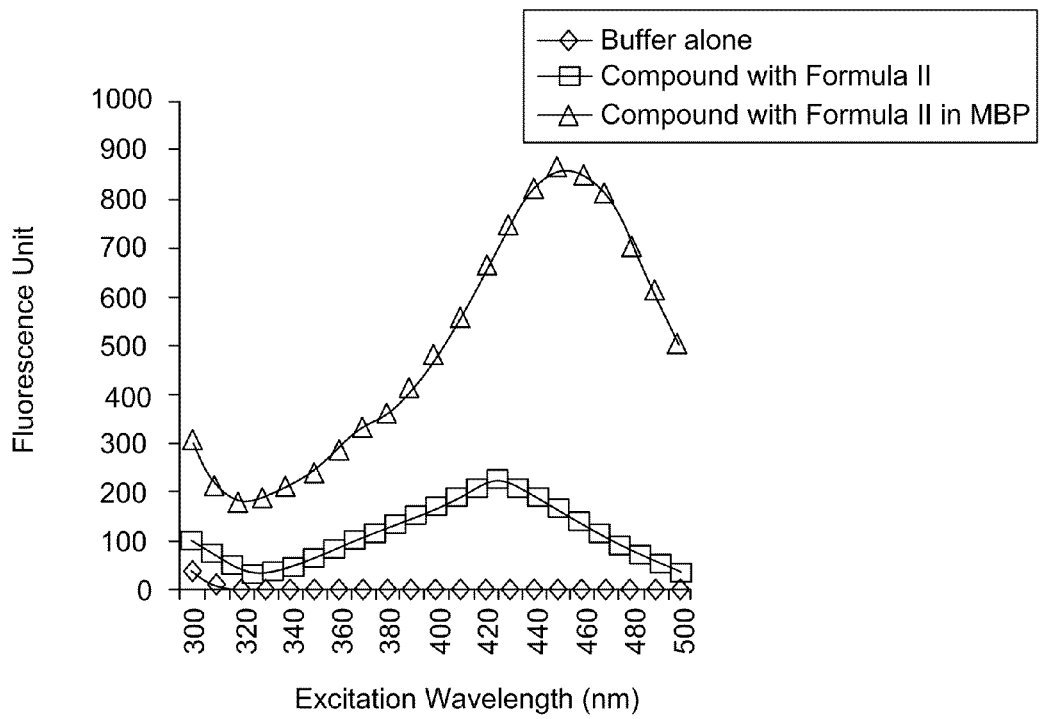
FIGS. 6A and 6B are excitation and emission spectra, respectively of compound having Formula II in the presence and absence of purified MBP.
Figure 6B:
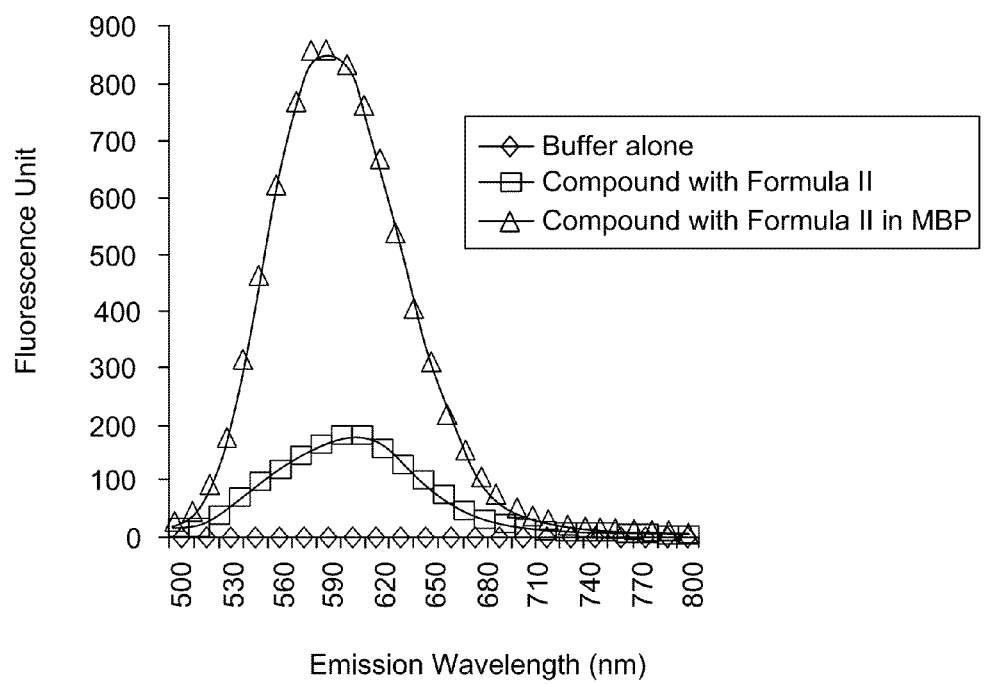
Figure 7:
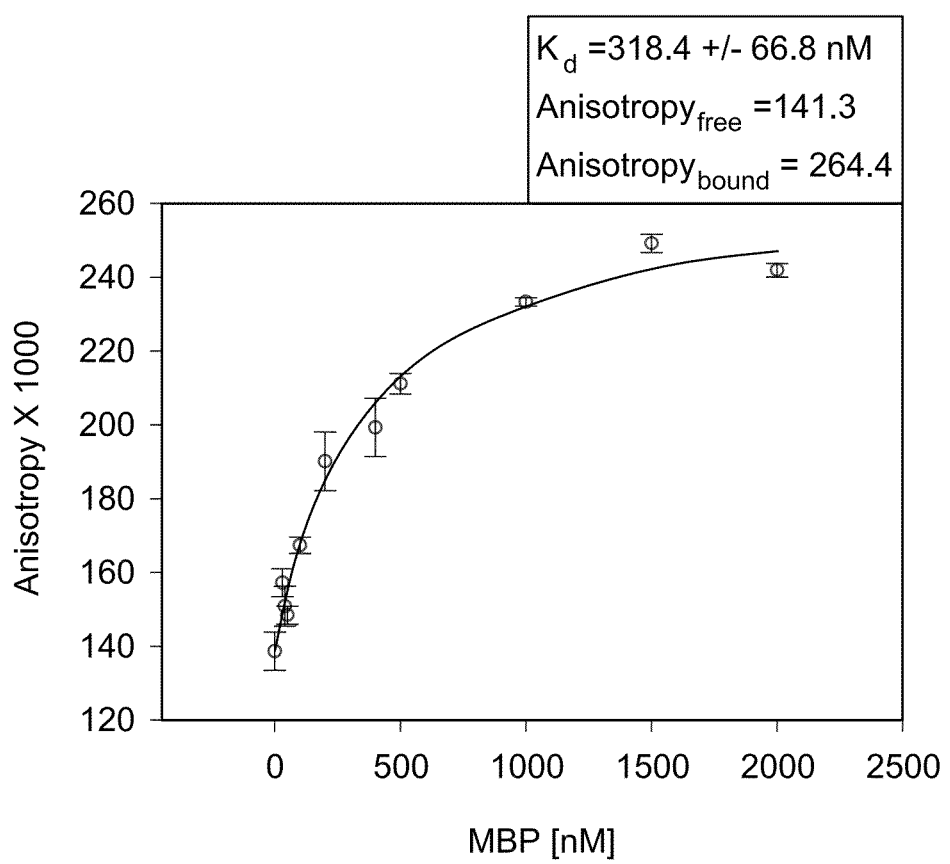
FIG. 7 is a graph showing binding affinity of compound having Formula II to purified MBP from an in vitro assay based on fluorescence polarization (FP).

Binding of the agent to MBP produces a significant increase in signal intensity as compared to unbound agent. In one or more embodiments, the agents exhibit preferential binding to MBP, a component of the myelinated nerves, which is determined by fluorescence spectroscopy and by fluorescence anisotropy, as shown in FIGS. 6A-B, and FIG. 7, respectively. These agents show a significant specificity for MBP.

The method of imaging nerves in a surgical field comprises detection of agents. The detection comprises applying a light source on the surgical site of the subject, wherein the light source is tuned to the spectral excitation characteristics of the compound of Formula I; and observing the surgical site of the subject through an optical filter tuned to the spectral emission characteristics of the compound of Formula I. In one or more embodiments, wherein the detecting is effected by gamma imaging, fluorescence microscopy, laser-confocal microscopy, cross-polarization microscopy, autoradiography, magnetic resonance imaging, magnetic resonance spectroscopy, or combination thereof.

A method of quantifying an amount of MBP present in a tissue sample, comprises contacting the tissue sample with an agent; and quantifying an amount of the agent present in the tissue sample by comparing to a baseline measurement of MBP in a control sample, wherein the agent comprises a compound of Formula I, a $^{13}$C enriched compound of Formula I, an $^{19}$F-labeled derivative of Formula I, a radioisotope derivative of Formula I or combinations thereof.

In some embodiments, the agent, which specifically binds to MBP, may be a radioisotope, a $^{13}$C enriched compound, or a $^{19}$F-labeled derivative. In some embodiments, a radioisotope derivative of the compound of Formula I may be prepared and imaging is accomplished through radioimaging. Alternatively, a $^{13}$C enriched compound of Formula I, or a $^{19}$F-labeled derivative of Formula I may be prepared.

The agent comprising the compound of Formula I, a $^{13}$C enriched compound of Formula I, an $^{19}$F-labeled-derivative of Formula I, or a radioisotope derivative of Formula I, may be detected by its emitted signal, such as a magnetic resonance signal or emitted radiation from a radioisotope derivative of Formula I, autofluorescence emission, or optical properties of the agent. The method of detection of agent comprising the compound of Formula I, a $^{13}$C enriched compound of Formula I, an $^{19}$F-labeled-derivative of Formula I, or a radioisotope derivative of Formula I, may include fluorescence microscopy, laser-confocal microscopy, cross-polarization microscopy, nuclear scintigraphy, positron emission tomography ("PET"), single photon emission computed tomography ("SPECT"), magnetic resonance imaging ("MRI"), magnetic resonance spectroscopy ("MRS"), computed tomography ("CT"), or a combination thereof, depending on the intended use and the imaging methodology is available to the medical or research personnel.

In one embodiment, the nerve labeling agent comprises a compound of Formula (X)

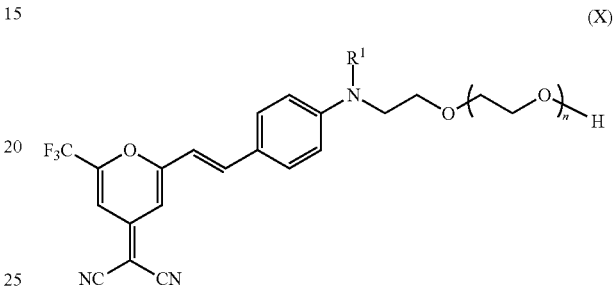

(X)

wherein $R^1$ is H, alkyl, hydroxyalkyl or alkoxy, and n is an integer between 1 to 4.

In some embodiments, the agents comprise compounds shown herein, in which the fluorine is present as a substituent on the amine moiety. Examples of such agents are provided below as Formula XI and XII wherein n is an integer between 0 and 3;

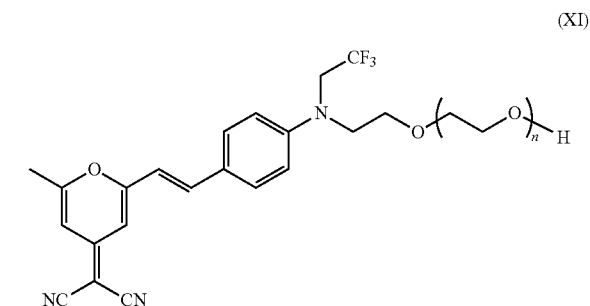

(XI)

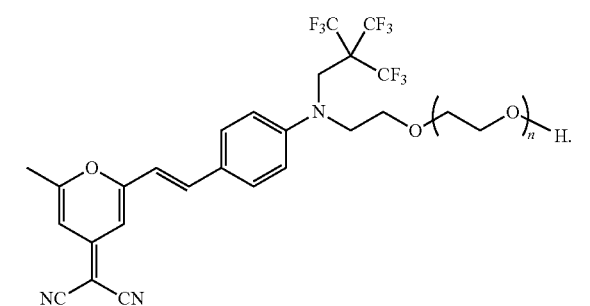

(XII)

The imaging methods described may be applicable to analytical, diagnostic, or prognostic applications related to MBP detection. The applications may be particularly applicable in intraoperative nerve labeling, spinal imaging, brain tissue imaging, non-invasive in vivo measurement of myelination levels, detection of myelin or MBP in biological fluid, and preclinical and basic neuroscience bench research aimed at the study of the function and process of myelination, and the dysfunction and repair of myelin.

In one embodiment, an agent which binds specifically to MBP may be administered parenterally to a surgical subject prior to surgery such that the agent binds to MBP and may be cleared from tissues that do not contain MBP. In another embodiment, the agent may be applied directly, via painting on, spraying on, or local injection to the surgical field during surgery, allowed to bind to MBP present, and the surgical site washed by lavage to clear unbound composition from the site. During surgery, a light source tuned to the spectral excitation characteristics of the agent may be applied to the surgical field. The agent may be observed through an optical filter tuned to its spectral emission characteristics. Due to their specific binding to the fluorescing agent, nerves and other myelin containing tissue are distinguishable from tissue not containing MBP. This enables the surgeon to avoid inadvertently cutting or damaging myelinated tissue by avoiding fluorescing tissue, or facilitates accurately administering treatment to the intended myelinated tissue. In certain embodiments the agent comprises the compound of Formula I.

An agent which specifically binds to MBP may be administered parenterally to a subject prior to surgery or prior to treatments targeting a nerve or other myelin containing tissue, such as pharmaceutical or surgical nerve block. In certain embodiments, the myelinated tissue may be part of the spinal canal and intervertebral foramen. In other embodiments, the myelinated tissue may be part of the brain. In certain embodiments the agent comprises the compound of Formula I, a $^{13}C$ enriched compound of Formula I, an $^{19}F$-labeled-derivative of Formula I, or a radioisotope derivative of Formula I.

In one embodiment an agent, such as one comprising the compound of Formula I, a $^{13}C$ enriched compound of Formula I, or an $^{19}F$-labeled-derivative of Formula I, may be administered parenterally to a surgical subject, prior to surgery, to permit binding to MBP, and clearance from tissues that do not contain MBP without the elimination of specific MBP binding.

In another embodiment, an agent which is a radioisotope and which specifically binds to MBP may be administered parenterally to a subject prior to treatment to allow binding and clearance from tissues that do not contain myelin. Imaging techniques such as nuclear scintigraphy, PET, SPECT, CT, MRI, MRS, or any combination thereof, may then be used to aid in differentiation of the myelin and non-myelin containing tissues and may employ a gamma camera, a scanner or a probe. The agent may be a radioisotope derivative of the compound of Formula I.

In another embodiment, an agent, such as one comprising the compound of a radioisotope derivative of Formula I, may be administered parenterally to a patient suspected of, or determined to be, suffering from a spinal pathology, such as but not limited to, spinal compression, spinal nerve root compression, or a bulging disc. After binding to spinal MBP, and clearance from tissue that does not contain MBP without eliminating the specific MBP binding, the spine may be imaged for in vivo using radioisotope imaging such as PET, SPECT, or any combination thereof.

By inspection of the diagnostic images, the clinician may determine if, and where, the spinal cord, or associated nerve roots, are impinged, such as by the vertebral column or foreign matter. Additional scans, such as CT or MRI, may also be conducted in conjunction with PET or SPECT scans, to provide additional information, such as the structure and relative positioning of elements of the vertebral column. In one embodiment, this method may be applied to a surgical procedure to image the spinal region intraoperatively.

In another embodiment, myelination level is accessed in vivo by imaging a radioisotope derivative of an agent, which binds specifically to MBP. The agent is administered parenterally to a subject diagnosed with, or suspected of having, a myelin-associated neuropathy. After binding to MBP, and clearance from tissue that does not contain MBP without eliminating specific MBP binding, components of the central or peripheral nervous system may be imaged by a method suitable for in vivo imaging of the radioisotope. Such methods include PET and SPECT. By inspection of the imaging results, the clinician may determine the amount of myelination, as reflected by levels and anatomical localization of signal emitted by the radioisotope derivative of the agent and detected by the appropriate imaging methodology. In certain embodiments, the agent is a radioisotope derivative of the compound of Formula I.

In one or more embodiments, to determine whether myelination in the patient may be deficient, myelination levels may be compared to those exhibited by a subject or subjects believed or known not to be suffering from a myelin-associated neuropathy. In another embodiment, rates of demyelination or remyelination may be determined Following treatment with a known or suggested therapeutic agent believed or anticipated to prevent or slow demyelination or to promote remyelination in patients suffering from myelin-associated neuropathies, myelination levels are evaluated by performing the imaging over time in the patients treated with the therapeutic agent. The imaging may be performed at different points of time and the level of myelination at one time point compared to that of another.

A positive result suggestive of a myelin-associated neuropathy may be one in which the decrease of MBP of the subject, compared to a baseline measurement of MBP in a control sample, is statistically significant. The control sample may be from a similar sample free of a myelin-associated neuropathy or from the same subject with measurements taken over time.

In yet another embodiment, biological fluid such as blood or cerebrospinal fluid may be contacted with an agent specific for binding to MBP. The fluorescence properties of the agent, such as anisotropy or fluorescence intensity, in the presence of the diseased sample may be compared to a control, non-diseased sample. For homogenous measurements based on fluorescence anisotropy or changes in intensity, the samples need not be washed to remove unbound agent.

In yet another embodiment, a biopsied mammalian tissue sample, or a tissue sample cultured in vitro, may be contacted with an agent specific for binding to MBP. The agent may comprise the compound of Formula I, a $^{13}C$ enriched compound of Formula I, or a $^{19}F$-labeled-derivative of Formula I. Contacting with the agent may be used to determine the location, presence, or amount of MBP in the tissue sample. The tissue sample may be sampled from a subject that has been experimentally manipulated so as to serve as a verified or purported model of myelin-associated neuropathy, or that has received at least one therapeutic agent verified as, or purported to be, a treatment for myelin-associated neuropathy. The therapeutic agent may be associated with the preclinical evaluation or basic neuroscience research aimed at studying the function and process of myelination, and the dysfunction and repair of myelin.

Fresh frozen cryostatic sections, or fixed or embedded sections or samples, of the biopsy or culture tissue sections, may be contacted with an agent specific for binding to MBP. The samples may be prepared using various sectioning techniques such as microtome, vibratome, or cryostat preparation. The agent may comprise the compound of Formula I, or a $^{13}$C enriched compound of Formula I, or an $^{19}$F-labeled-derivative of Formula I.

After binding to MBP, the sample may be washed in a manner and medium suitable to remove any unbound and non-specifically bound label from the sample, without eliminating specific binding to MBP.

Any of a number of detection, visualization, or quantitation techniques, including but not limited to fluorescence microscopy, laser-confocal microscopy, cross-polarization microscopy, autoradiography, MRI, MRS, or other applicable methods, or any combination thereof, may be then be used to assess the presence or quantity of an agent having specific binding to MBP in the tissue sample and may represent the presence or amount of MBP. In certain embodiments, the agent may comprise the compound of Formula I, a $^{13}$C enriched compound of Formula I, or a $^{19}$F-labeled-derivative of Formula I. The labeling with, and detection, visualization, or quantitation of the agent, may also be performed in conjunction with labeling with, and detection, visualization, or quantitation of at least one other compound that specifically binds a substance other than MBP.

In one or more embodiments, a kit for detecting myelin-associated neuropathy in a subject, comprises an agent, and a pharmaceutically acceptable carrier, wherein the agent comprises a compound of Formula I, a $^{13}$C enriched compound of Formula I, a $^{19}$F-labeled derivative of Formula I, or a radioisotope derivative of Formula I.

EXAMPLES

The following non-limiting Examples are shown and describe various embodiments of the present invention. Various compounds were synthesized and tested for specific binding to in vitro or in vivo samples containing myelin. The compounds were used to compare binding and optical properties. The desired compounds were prepared according to the scheme below

TABLE 1

Different reactants were used to form different products using synthetic scheme (I)

| Reactant | Reactant (2) | Product (3) |
|---|---|---|
| 1 | 2a: $R^1$ = H, $R^2$ = Boc, $R^3$ = H | 3a: $R^1$ = $R^2$ = $R^3$ = H |
| 1 | 2b: $R^1$ = H, $R^2$ = $CH_2CH_2OH$, $R^3$ = H | 3b: $R^1$ = H, $R^2$ = $CH_2CH_2OH$, $R^3$ = H |
| 1 | 2c: $R^1$ = H, $R^2$ = Boc, $R^3$ = OMe | 3c: $R^1$ = $R^2$ = H, $R^3$ = OMe |
| 1 | 2d: $R^1$ = Boc, $R^2$ = 4-BocNHBz, $R^3$ = OMe | 3d: $R^1$ = H, $R^2$ = 4-$NH_2$Bz, $R^3$ = OMe |

Synthetic Scheme for Making Intermediate 2c

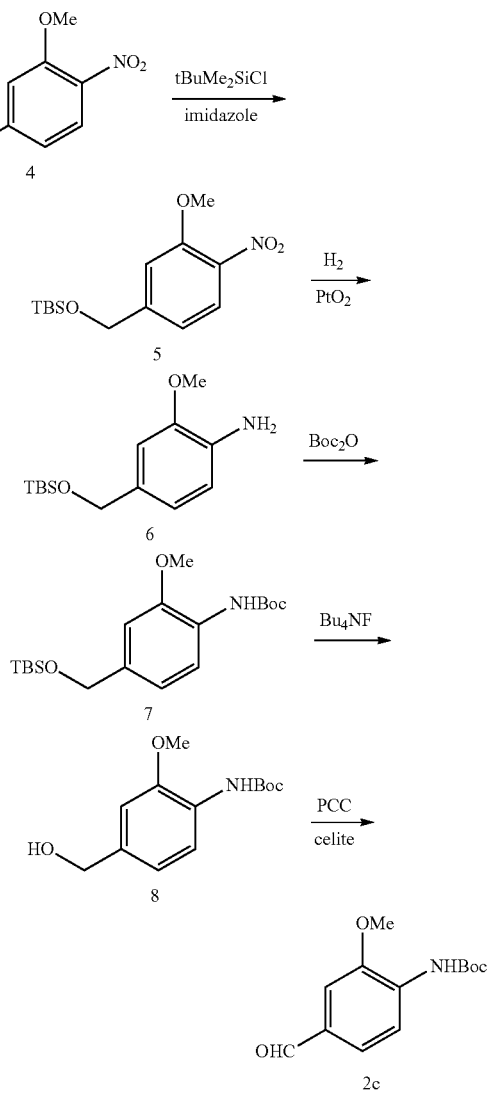

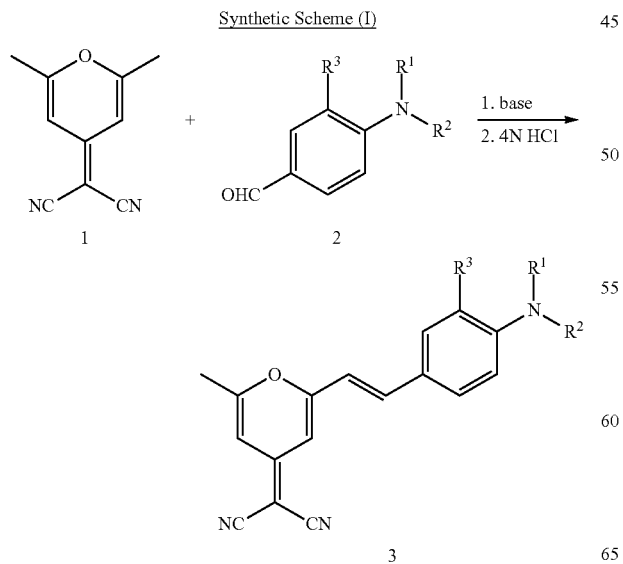

Synthetic Intermediate for Making Intermediate 2d

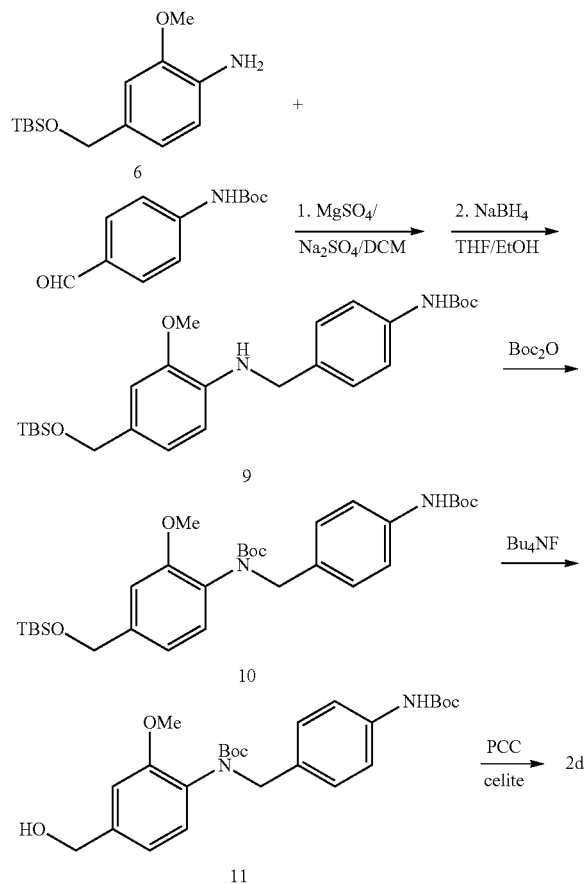

Example 1

Synthesis of tert-butyl(3-methoxy-4-nitrobenzyloxy) dimethylsilane (5)

To a solution of 3-methoxy-4-nitrobenzyl alcohol (2.15 g, 11.75 mmol) and imidazole (880 mg, 12.94 mmol) in dry dichloromethane (58 ml) at 0° C. was quickly added tert-butyldimethylchlorosilane in one portion and the mixture was stirred at for 1 hour. LC-MS analysis indicated complete conversion. The solution was washed with ice cold water (50 ml) dried over $Na_2SO_4$, adsorbed on silicagel and purified by HPLC with hexanes/ethyl acetate 20-30% gradient to give compound 5 as a light yellow solid (3.3 g, 94%). MS (EI+): 282 (M-Me); 240 (M-tBu); H-NMR (400 MHz, $CD_2Cl_2$): 7.85 (1H, d, J=8 Hz) 7.19 (1H, s) 6.98 (1H, dq, J=8 Hz, 0.4 Hz) 4.82 (2H, s) 3.99 (3H, s) 1.0 (9H, s) 0.17 (6H, s). C-NMR (400 MHz, $CD_2Cl_2$): 153.96, 150.05, 138.73, 126.32, 117.74, 111.26, 64.65, 57.06, 26.30, 18.90, −4.97.

Example 2

Synthesis of 4-((tert-butyldimethylsilyloxy)methyl)-2-methoxyaniline (6)

A suspension of $PtO_2$ (330 mg) in ethyl acetate (21 ml) was purged with $H_2$ and hydrogenated at room temperature overnight. To this suspension was added, via canula, compound 5 (3.3 g) in 12 ml ethyl acetate and the mixture was stirred at room temperature under $H_2$ for 4 hrs. The catalyst was filtered off through a 0.4-micron membrane and the solvent was removed under vacuum to give the desired product as a crystalline white waxy solid (2.673 g, 85%). H-NMR (400 MHz, $CD_2Cl_2$): 6.99 (1H, d, J=8 Hz) 6.78 (1H, s) 6.52 (1H, dd, J=6 Hz, 0.8 Hz) 6.02 (1H, brs) 4.76 (2H, s) 3.89 (3H, s) 0.99 (9H, s) 0.16 (6H, s). C-NMR (400 MHz, $CD_2Cl_2$): 151.02, 147.1, 135.23, 122.42, 118.34, 110.86, 67.35, 56.02, 26.20, 19.20, −2.05.

Example 3

Synthesis of tert-butyl 4-((tert-butyldimethylsilyloxy)methyl)-2-methoxyphenylcarbamate (7)

To a solution of amine 6 (180 mg, 0.67 mmol) in THF/water (2.1 ml/0.52 ml) was added Boc anhydride (162 mg, 0.74 mmol) and $NaHCO_3$ (85 mg, 1.01 mmol). The mixture was stirred at room temperature overnight, then extracted with ethyl acetate, adsorbed on silica and purified by MPLC with hexanes/ethyl acetate 0-20% gradient to give compound 7 (242.4 mg, 98%).

Example 4

Synthesis of tert-butyl 4-(hydroxymethyl)-2-methoxyphenylcarbamate (8)

To a solution of protected alcohol 7 (242.4 mg, 0.66 mmol) in THF (2.5 ml) was added a solution of 1M tetrabutylammonium fluoride in THF (0.73 ml, 0.73 mmol) and the mixture was stirred at room temperature for 24 hrs. The crude product was adsorbed on silica gel and purified by MPLC, eluting with hexanes/ethyl acetate 40%-50% gradient to give the title alcohol (92.9 mg, 56% yield). H-NMR (400 MHz, $CD_2Cl_2$): 8.85 (1H, brs) 7.78 (1H, d, J=8 Hz) 7.09 (1H, s) 6.82 (1H, dd, J=8 Hz, 0.4 Hz) 4.58 (2H, d, J=4 Hz) 3.5 (1H, t, J=4 Hz) 1.18 (9H, s).

Example 5

Synthesis of tert-butyl 4-((4-((tert-butyldimethylsilyloxy)methyl)-2-methoxyphenylamino)methyl)phenylcarbamate (9)

To a solution of the amine 6 (91 mg, 0.34 mmol) and tert-butyl 4-formylphenylcarbamate (75 mg, 0.34 mmol) in dry dichloromethane (1.7 ml) was added a finely ground 1:1 mixture of $MgSO_4$ and $Na_2SO_4$ (20 mg) and the mixture was stirred under $N_2$ at room temperature for 3 days. The suspension was filtered through a 0.4 micron Whatman™ cartridge (GE Healthcare Biosciences, Pittsburgh, Pa.), the solvent was removed with a stream of dry $N_2$ and the remaining red oil was dissolved in 1.2 ml dry THF and 0.2 ml anhydrous EtOH. Under vigorous stirring, sodium borohydride (14 mg, 0.37 mmol) was added and the mixture was stirred at room temperature for 30 min. Water (100 µl) was added and the solvent was stripped with a stream of $N_2$. THF (1.5 ml) was added, the mixture was filtered through a 0.4 micron Whatman cartridge, dried with a stream of $N_2$ and used crude in the next step.

Example 6

Synthesis of tert-butyl 4-(((4-((tert-butyldimethylsilyloxy)methyl)-2-methoxyphenyl)(tert-butyloxycarbonyl)amino)methyl)phenylcarbamate (10)

The crude product 9 (0.34 mmol) was dissolved in THF (1 ml) and water (0.2 ml). Under vigorous stirring, Boc anhydride (162 mg, 0.74 mmol) and $NaHCO_3$ (72 mg, 0.86 mmol) were added in portions over 2 days and the mixture was stirred for a total of 3 days at room temperature. The crude product was adsorbed on silicagel and purified by MPLC eluting with hexanes/ethyl acetate 0-25% gradient. Yield: 182 mg (91%) LCMS ESI+: m/z 595 (M+Na+).

Example 7

Synthesis of tert-butyl 4-(((tert-butyloxycarbonyl)(4-(hydroxymethyl)-2-methoxyphenyl)amino)methyl) phenylcarbamate (11)

To a solution of compound 11 (182 mg, 0.32 mmol) in dry THF (1.2 ml) was added a solution of tetrabutylammonium fluoride (1.0 M, 0.38 ml) and the mixture was stirred at room temperature for 12 hours. The solvent was removed with a stream of $N_2$ and the mixture was advanced without purification to the next step.

Example 8

Synthesis of tert-butyl 4-formyl-2-methoxyphenylcarbamate (2c)

To a stirred suspension of finely ground PCC (80 mg, 0.56 mmol) and Celite (80 mg) in dry dichloromethane (2 ml) at room temperature was added drop wise a solution of the alcohol 8 (92.9 mg, 0.37 mmol) in dichloromethane (1 ml followed by 0.7 ml rinse). The mixture was stirred in the dark for 20 minutes. The reaction mixture was adsorbed on silica gel and purified by normal phase MPLC, eluting with hexanes/ethyl acetate 20-40% gradient. GC-MS EI+: m/z 251 (M+); LC-MS ESI+: m/z 252 (M+H+). Yield: 72.7 mg (78%). H-NMR (400 MHz, CD2Cl2): 9.06 (1H, brs) 8.02 (1H, d, J=8 Hz) 7.65 (1H, s) 6.92 (1H, dd, J=8 Hz, 0.4 Hz) 4.67 (1H, s) 1.22 (9H, s).

Example 9

Synthesis of tert-butyl 4-(((tert-butyloxycarbonyl)(4-formyl-2-methoxyphenyl)amino)methyl)phenylcarbamate (2d)

To a solution of compound 11 from previous step (0.32 mmol) in dry dichloromethane (2.4 ml) was added a finely ground mixture of PCC (76 mg, 0.35 mmol) and Celite (76 mg) and the mixture was stirred at room temperature in the dark for 90 min. The crude product was adsorbed on silica gel and purified by MPLC, eluting with hexanes/ethyl acetate 0-40% gradient, to give the title compound as a white waxy solid, 80.3 mg (51.7% from compound 9). LCMS ESI+: 479 (M+Na+). H-NMR (400 MHz, $CD_2Cl_2$): 9.90 (1H, s) 7.39 (1H, d, J=0.4 Hz) 7.33 (1H, dd, J=8 Hz, J=0.4 Hz) 7.24 (2H, d, J=12 Hz) 7.06-7.14 (3H, m) 6.58 (1H, brs) 4.73 (2H, brs) 3.86 (3H, s) 1.48 (9H, s) 1.37 (9H, brs). C-NMR (400 MHz, CD2Cl2): 191.86, 156.26, 155.08, 153.14, 138.28, 137.44, 136.58, 133.16, 130.46, 129.41, 124.10, 118.58, 110.69, 80.78, 56.22, 52.65, 28.58, 28.46.

Example 10

Synthesis of (E)-2-(2-(4-(4-aminobenzylamino)-3-methoxystyryl)-6-methyl-4H-pyran-4-ylidene)malononitrile (3d)

A mixture of 2-(2,6-dimethyl-4H-pyran-4-ylidene) malononitrile (1, 16.5 mg, 96 µmol) and aldehyde 2d (34.9 mg, 76.5 µmol) were dissolved in anhydrous EtOH (0.5 ml) at 65 C. Piperidine (1 µl) was added and the mixture was stirred at 80° C. for 6 hrs. The solvent was removed with a stream of $N_2$ and the crude mixture was purified by reverse phase HPLC using water/acetonitrile 40-100% gradient. Yield: 8.1 mg (17.4%). LCMS: m/z 611 (M+H+), 623 (M+Na+). H-NMR (400 MHz, $CD_2Cl_2$): 7.45 (1H, d, J=16 Hz) 7.29 (2H, d, J=12 Hz) 7.17 (2H, d, J=8 Hz) 7.03-7.12 (2H, m) 6.69-6.79 (2H, m) 6.52-6.61 (2H, m) 4.76 (2H, brs) 3.89 (3H, s) 2.43 (3H, s) 1.52, (9H, s) 1.41 (9H, brs). C-NMR (400 MHz, $CD_2Cl_2$): 162.54, 159.01, 156.35, 152.56, 137.61, 137.21, 134.39, 133.06, 132.89, 128.82, 120.38, 118.39, 117.99, 115.03, 114.99, 107.37, 106.31, 80.21, 58.97, 55.49, 29.68, 28.00, 27.93, 19.75. The purified product (8.1 mg) was treated with a 4N HCl solution in dioxane (4 N, 0.65 ml) for 3 hrs. The mixture was diluted with hexanes, the precipitate centrifuged, re-suspended and washed with hexanes, then dried under vacuum. LCMS ESI+ m/z: 411 (M+H+). H-NMR (400 MHz, DMSO-D6) 7.22-7.28 (5H, m) 6.83-6.89 (2H, m) 6.65 (1H, d, J=16 Hz) 6.54 (1H, d, J=16 Hz) 5.54 91H, s) 5.32 (1H, s) 4.22-4.38 (2H, brs) 3.92 (3H, s) 2.39 (3H, s).

Example 11

Synthesis of (E)-2-(2-(4-amino-3-methoxystyryl)-6-methyl-4H-pyran-4-ylidene)malononitrile (3c)

A mixture of 2-(2,6-dimethyl-4H-pyran-4-ylidene)malononitrile (1, 20.7 mg, 0.12 mmol) and aldehyde 2c (25.1 mg, 0.1 mmol) were dissolved in anhydrous EtOH (0.67 ml) at 65° C. Piperidine (0.5 µl) was added and the mixture was stirred at 80° C. for 7 hours. The solvent was removed with a stream of $N_2$, the crude mixture was dissolved in EtOAc at 5 mg/ml and purified by normal phase preparative HPLC using hexanes/ethyl acetate as eluent. Yield: 10.6 mg (26%). LCMS ESI+m/z 406 (M+H+) H-NMR (400 MHz, $CD_2Cl_2$): 8.16 (1H, d, J=8 Hz) 7.47 (1H, d, J=16 Hz) 7.29 (1H, s) 7.19 (1h, dd, J=8 Hz, 0.4 Hz) 7.1 (1H, d, J=0.4 Hz) 6.67-6.74 (2H, m) 6.56 (1H, m) 3.97 (3H, s) 2.43 (3H, s) 1.55 (9H, s). C-NMR (400 MHz, $CD_2Cl_2$) 163.02, 160.11, 157.01, 152.81, 148.32, 138.31, 131.33, 129.29, 122.99, 118.01, 116.81, 115.74, 108.45, 107.26, 106.77, 81.27, 56.35, 28.56, 20.31. This compound was treated with a 4N HCl solution in dioxane (4 N, 1.3 ml) for 3 hrs. The mixture was diluted with hexanes, the precipitate centrifuged, re-suspended and washed with hexanes, then dried under vacuum. LCMS ESI+ m/z: 306 (M+H+). H-NMR (400 MHz, $CD_2Cl_2$) 7.37 (1H, d, J=16 hz) 7.12 (1H, dd, J=16 Hz, 0.4 Hz) 7.02 (1H, d, J=0.4 Hz) 6.56-6.63 (3H, m) 6.12 (1H, m) 3.97 (3H, s) 2.42 (3H, s). C-NMR (400 MHz, $CD_2Cl_2$) 164.58, 156.12, 151.52, 140.90, 139.05, 129.73, 127.19, 121.74, 115.48, 110.73, 109.95, 102.81, 101.68, 100.79, 90.2, 55.89, 21.02.

Example 12

Synthesis of (E)-2-(2-(4-(2-hydroxyethylamino) styryl)-6-methyl-4H-pyran-4-ylidene)malononitrile (3b)

A mixture of 2-(2,6-dimethyl-4H-pyran-4-ylidene)malononitrile (1, 190 mg, 1.1 mmol) and aldehyde 2b (156.5 mg, 95%, 0.9 mmol) were dissolved in anhydrous EtOH (5 ml) at 65 C. Piperidine (5 μl) was added and the mixture was stirred at 80 C for 4 hrs. The solvent was removed with a stream of $N_2$, the crude mixture was dissolved in $CH_3CN$ and purified by reverse phase preparative HPLC using water/acetonitrile gradient. Yield: 123 mg (43%). LCMS $ESI^+$ m/z 320 ($M+H^+$) H-NMR (400 MHz, acetone-D6) 7.54, (1H, s) 7.52 (2H, d, J=8 Hz) 6.91 (1H, d, J=16 Hz) 6.72 (2H, d, J=8 Hz) 6.65 (1H, d, J=0.4 Hz) 6.55 (1H, s) 5.67 91H, brs) 3.90 (1H, brs) 3.75 (2H, t, J=8 Hz) 3.31 (2H, q, J=8 Hz) 2.49 (3H, s). C-NMR (400 MHz, acetone-D6): 163.20, 161.24, 156.66, 151.42, 139.01, 131.73, 129.96, 123.09, 115.24, 112.39, 105.37, 104.77, 60.15, 55.81, 45.55, 18.82.

Example 13

Synthesis of (E)-2-(2-(4-aminostyryl)-6-methyl-4H-pyran-4-ylidene)malononitrile (3a)

A mixture of 2-(2,6-dimethyl-4H-pyran-4-ylidene)malononitrile (1, 190 mg, 1.1 mmol) and aldehyde 2a (200 mg, 0.9 mmol) were dissolved in anhydrous EtOH (5 ml) at 65° C. Piperidine (5 μl) was added and the mixture was stirred at 80° C. for 5 hours. The solvent was removed with a stream of $N_2$, the crude mixture was dissolved in EtOAc at 5 mg/ml and purified by normal phase preparative HPLC using hexanes/ethyl acetate as eluent. Yield: 132 mg (39%). A portion of this compound (68.4 mg, 0.18 mmol) was treated with a 4N HCl solution in dioxane (4N, 9 ml) for 3 hours. The mixture was diluted with hexanes, the precipitate centrifuged, re-suspended and washed with hexanes, then dried under vacuum to give the title dye as hydrochloride (50.4 mg, 90%). LCMS $ESI^+$ m/z: 276 ($M+H^+$). H-NMR (400 MHz, DMSO) 7.52 (1H, dd, J=16 Hz, J=2 Hz) 7.4 (2H, m) 6.96 (1H, m) 6.58-6.72 (4H, m) 2.42 (3H, s). C-NMR (400 MHz, DMSO) 164.16, 161.71, 160.47, 157.07, 139.47, 130.61, 122.72, 116.82, 114.31, 112.62, 105.89, 105.25, 54.39, 19.81.

Example 14

Measurement of Optical Properties of the Nerve Labeling Agents

The flurophores were dissolved in dimethylsulfoxide (DMSO) to make a 10 mM stock solution. An aliquot was taken to prepare a 10-100 μM flurophore solution in methanol, water, or DMSO. Optical measurements from the three solvents were taken. Absorbance spectra were measured using a PerkinElmer Lambda™ 20 UV/VIS spectrometer (PerkinElmer, Waltham, Mass.). Emission spectra were generated using a PTI steady state fluorimeter (Photon Technology International, Birmingham, N.H.). The stoke shift for nerve labeling agents on Table 3 are greater than 100 nm.

TABLE 3

Optical properties of the nerve labeling agents (compounds) in DMSO.

| Solvent Compounds | DMSO | | |
|---|---|---|---|
| | Absorbance Maximum (nm) | Emission Maximum (nm) | Stoke shift |
| Formula II | 478 | 607 | 129 |
| Formula V | 484 | 618 | 134 |
| Formula III | 491 | 623 | 132 |
| Formula IV | 492 | 642 | 150 |
| Formula VI | 478 | 631 | 153 |

Example 15

In Vivo Imaging

All procedures were approved by the Institutional Animal Care and Use Committee (IACUC) at GE Global Research. Male CD-1 mice ranging in body weight from 25-30 g and SD rats (250-350 g) were purchased from Charles River Laboratories (Wilmington, Mass.) and housed at 22-23° C. on a 12-hour light/dark cycle. On the day of the experiment, rodents were anesthetized using 2-4% isofluorane and given a single tail vein injection of either imaging agent in formulation or formulation excipients alone. Imaging agents were prepared for IV administration in a buffer containing: 0-0.5% DMSO (Sigma D8418), 10-40% Propylene Glycol (Fisher P355-1), 1-40% Polyethylene Glycol (PEG-300; Sigma 202371), 0-25% 2-Hydroxypropyl-3-Cyclodextrin (2-HP-βCD, Sigma H5784) brought to the desired final volume in sterile water (Sigma W3500). No preservative system was used as formulated doses were injected on the same day. The rodents were then returned to the home cage until the designated time point for imaging.

In vivo imaging consisted of detailed fluorescence emission characterization and surgical imaging using a Zeiss Lumar™ imaging system (Carl Zeiss Inc. Thornwood, N.Y.) with coupled multispectral imaging camera (Nuance camera; CRI, Woburn, Mass.) or AxioCam™ (Carl Zeiss Inc. Thornwood, N.Y.). The Zeiss Lumar imaging instrument was used in both the dosing and kinetics studies. A variety of excitation filters were used to characterize the in vivo fluorescence of these agents. These filters included (filter center/bandwidth): 406/15 nm, 460/60 nm, 472/30 nm, 475/35 nm, 473/10 nm and 488/10 nm. Fluorescence emission data was then recorded at wavelengths ranging from 420 to 720 nm at 10 nm steps using the attached CRI-Nuance™ camera (Cambridge Research and Instrumentation Inc., Wobur, Mass.) or using a 500 nm-long pass filter on the AxioCam. Fluorescence images were collected using exposure times of 5 seconds in both control and agent injected animals for normalization.

Example 16

Dosing Study for Formula II

The dose response for Formula II was determined in adult male CD-1 mice. In the dose-response study, each animal received a single dose of Formula II approximately 0.5 hour prior to imaging of key nerves. Doses of Formula II in this study ranged from 0.2 to 16.6 mg/kg. Control mice were given a single injection of the IV formulation (vehicle only) and measured to determine background fluorescence. Post-processing of imaging data included line profile analysis to determine the fluorescence maxima of nerves and adjacent muscle and adipose tissue sample. The fluorescence maxima were measured in two regions of each nerve and surrounding muscle tissue to display the average nerve-to-muscle ratio (N:M), as shown FIG. 1.

Example 17

Kinetics of Formula II

Following the determination of an optimal dosing in the CD-1 animal model (FIG. 1), a separate study was performed to determine the overall pharmacokinetics of Formula II, as shown in FIG. 2. Each mouse (CD-1) received a single injection accounting for a dose of 3.33 mg/kg Formula II and was euthanized at 0.5, 1, 2 and 3 hours post injection. Key nerves were then dissected and imaged. Control mice were used, where only a single injection of IV formulation buffer was given.

Example 18

Pre-Clinical Imaging of Formula II in a Large Rodent Model

Formula II was formulated for IV injection in a 310 g Sprague Dawley (SD) rat using the following formulation excipients: 0.5% DMSO, 20% PEG-300, 30% Propylene Glycol and 25% 2-Hydroxypropyl-B-cyclodextrin. Each SD rat received a single injection of Formula II at the following doses-16.67 mg/kg (FIG. 3B) and 8.33 mg/kg (FIG. 3C). Formula II Control rats used were given a single injection of the IV formulation buffer only with no Formula II present (FIG. 3A). Animals were euthanized 0.5 hours post IV injection and key nerves were dissected and imaged. Visible nerves present (in FIGS. 3B-C) are indicated by an arrow. No visible nerves were seen in animals receiving a single dose of IV formulation only (Control; FIG. 3A).

Example 19

The Effect of Formulation on Tissue-Specific Fluorescence Imaging

Rats were given a single IV injection of 8.33 mg/kg Formula II formulated in 0.5% DMSO, 20% PEG-300, 30% Propylene Glycol with varying concentrations of 2-HPβCD (FIG. 4A—10%; FIG. 4B—15% and FIG. 4C—25%) and the images were collected 0.5 hours post IV injection. Varying concentrations of 2-HPβCD were used to assess the impact of agent kinetics. The addition of greater concentrations of 2-HPβCD increases the total formation of an inclusion complex between Formula II and the internal pore of 2-HPβCD, a cyclic oligosaccharide. This can effectively slow the kinetics of the drug distribution in vivo by reducing the free-to-bound drug ratio post-IV injection. Tissue specific fluorescence in the sciatic nerve (indicated by a single arrow) and adjacent muscle are shown in FIGS. 4A to 4C.

Example 20

Preparation of Nerve Tissue Sections for Ex Vivo Study

For ex vivo histological evaluation, various nerves including sciatic, femoral and trigeminal were harvested from male Sprague Dawley (SD) rats. Tissue was fixed by perfusion and/or post-fixed with formalin. Nerves were then flash-frozen using methanol and dry ice in OCT media. In some cases, polyvinylidene fluoride membranes were used to help keep the nerves vertical in the OCT media. Thin sections (5-10 microns) were sliced on a Leica microtome and stored in a −80° C. freezer prior to staining with antibodies or fluorescent dyes.

Example 21

Ex Vivo Binding of Nerve Labelling Agents to Sciatic Nerves

Nerve sections were prepared as described above. At the time of staining the slides were removed from −80° C. and allowed to come to room temperature. The nerves were fixed in neutral buffered formalin (10%) for 5 min after which the slides were rinsed in 1×PBS (3×, 5 min/each). 10 µM, or 20 µM each Formula II, Formula III, Formula IV, Formula V, or Formula VI was added onto the tissue in a formulation containing 10% Cremophor EL and 60% rat serum made in 1×PBS. The slides were incubated for 1 hour in a dark, moist/humid chamber at room temperature after which they were washed 3 times for 5 min/each in 1×PBS, cover-slipped, and imaged using the appropriate filter cube on a Zeiss Axioimager at 200× magnification. The binding of the agents and a control (with no agent) to the sciatic nerve sections are shown in FIG. 5.

Example 22

Isolation of Native MBP from Bovine Brain

Purified MBP from bovine brain was used for further evaluation of fluorophore binding. MBP in its native lipid-bound form was purified according to published protocols (Riccio et al. 1994; Riccio et al. 1990; Riccio et al. 1984) and was provided by Prof. Paolo Riccio from the University of Bari, Italy.

Example 23

Fluorescence measurements of Formula II binding to purified MBP

The excitation and emission spectra of Formula II were taken using the fluorescence mode of SpectraMax® M5 (Molecular Devices, Sunnyvale, Calif.). 10 µM Formula II was dissolved in the binding buffer (consisting of 0.25% CHAPS in 20 mM Tris, pH 7.5). Purified native MBP was added to a final concentration of 1.6 µM. The spectra for buffer alone, Formula II alone, and Formula II in the presence of purified MBP were taken, which are shown in FIGS. 6A and 6B.

Example 24

Binding Study of the Formula II to Purified MBP Via a Fluorescence Polarization (FP) Assay The FP binding assays were performed by mixing increasing amounts of native MBP with a fixed concentration of Formula II in Costar® 96-well black polystyrene plates (Corning Inc., Corning, N.Y.)) and the binding curve is shown in FIG. 7. Protein and fluorescent ligand dilutions were made in 0.25% CHAPS in 20 mM Tris (pH 7.5) which also served as the binding buffer. The reagents were allowed to incubate at room temperature for 10 min after which raw S (fluorescence intensity in the parallel direction) and P (fluorescence intensity in the perpendicular direction) values were measured at $\lambda_{max}$ for excitation (450 nm) and emission (590 nm) of Formula II in the presence of native MBP using the fluorescence polarization mode of Spectra Max M5 (Molecular Devices). The binding constant is determined as 318.4 from the binding curve of FIG. 7, results from the fluorescence anisotropy. The raw S and P values were used to calculate $Y_{obs}$ (observed anisotropy) using the equation=$[(S-P)/(S+2P)] \times 1000$.

Calculation of the $K_d$, $Y_{bound}$ and $Y_{free}$ values were performed using the equation below:

$$Y_{obs} = Y_{free} + (Y_{bound} - Y_{free}) \frac{K_d + Ct + F - \sqrt{(K_d + Ct + F)^2 - 4Ct \times F}}{2F}$$

wherein $Y_{free}$=anisotropy of the free fluorophore; $Y_{bound}$=anisotropy of the bound fluorophore; $K_d$=dissociation constant; Ct=MBP concentration used in the assay; F=concentration of the fluorophore used in the assay. $Y_{obs}$ (observed anisotropy) was calculated at each Ct (MBP concentration) using the raw S and P values, and F (concentration of fluorophore) is known. The equation is solved via non-linear regression using SigmaPlot™ version 11.2 (Systat Software Inc., San Jose, Calif.) to obtain the $K_d$, $Y_{bound}$, and $Y_{free}$ values.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of detecting myelin-associated neuropathy, comprising:
   administering an agent to a subject at risk of or diagnosed with a myelin-associated neuropathy, wherein said agent;
   binds to myelin basic protein (MBP); and
   comprises a compound of Formula I, a $^{13}$C enriched compound of Formula I, a $^{19}$F-labeled derivative of Formula I, or a radioisotope derivative of Formula I or combinations thereof;

wherein $R^1$ and $R^2$ are independently at each occurrence a hydrogen, hydroxyl group, $C_1$-$C^{30}$ aliphatic radicals, $C_3$-$C_{30}$ cycloaliphatic radicals, or $C_2$-$C_{30}$ aromatic radicals with the proviso that $R^1$ and $R^2$ are not both equal to a hydroxyl group;

$R^3$ is hydrogen, a hydroxyl group, an alkoxy group, a $C_1$-$C_6$ hydroxyalkyl group, a $C_1$-$C_6$ alkyl group or a substituted alkyl group; and the summation of alkyl groups of $R^1$, $R^2$ and $R^3$ is less than or equal to 16 carbon atoms; and determining myelination by detecting the agent resided in the subject, quantifying an amount of the agent resided in the subject, and comparing the amount of the agent resided in the subject with an amount of the agent resided in a control sample administered with the same agent, whereby the amount of the agent resided in the subject compared to the control sample is indicative of a myelin-associated neuropathy.

2. The method of claim 1, wherein $R^3$ is hydrogen, an alkyl group of from 1 to 6 carbon atoms, or an alkoxy group.

3. The method of claim 1, wherein at least one of the $R^1$ and $R^2$ is hydrogen, $C_1$-$C_{30}$ aliphatic radicals, and $C_2$-$C_{30}$ aromatic radicals.

4. The method of claim 1, wherein the $R^1$ is hydrogen and $R^2$ is a 4-aminobenzyl group.

5. The method of claim 1, wherein $R^1$ is hydrogen and $R^2$ is a hydroxyethyl group.

6. The method of claim 1, wherein $R^1$ and $R^2$ are hydroxyethyl groups.

7. The method of claim 1, wherein both $R^1$ and $R^2$ are hydrogen.

8. The method of claim 1, wherein the agent crosses the blood brain barrier (BBB).

9. The method of claim 1, wherein the agent crosses the blood nerve barrier (BNB).

10. The method of claim 1, wherein a molecular weight of the compound of Formula I is less than or equal to 500 Da.

11. The method of claim 1, wherein a Log P value of the compound of Formula I is less than or equal to 5.

12. The method of claim 1, wherein the compound of Formula I is

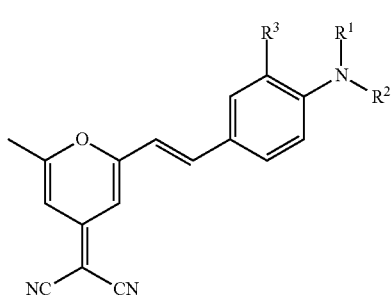

(I)

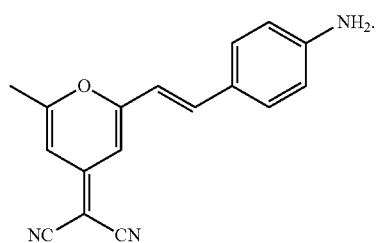 [SMILES: CC1=CC(=C(C#N)C#N)C=C(/C=C/c2ccc(N)cc2)O1]

13. The method of claim 1, wherein the compound of Formula I is

14. The method of claim 1, wherein the compound of Formula I is

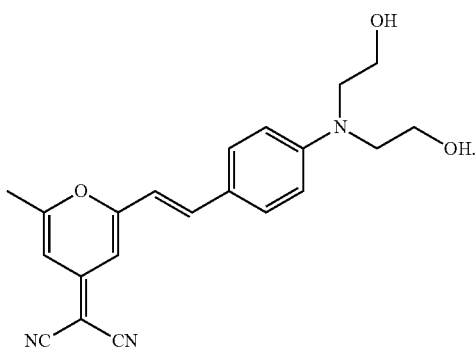 [SMILES: CC1=CC(=C(C#N)C#N)C=C(/C=C/c2ccc(N(CCO)CCO)cc2)O1]

15. The method of claim 1, wherein the compound of Formula I is

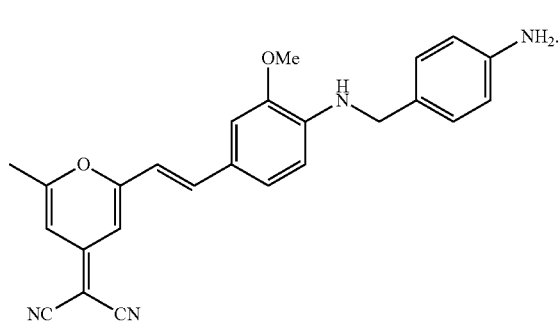 [SMILES: COc1cc(/C=C/C2=CC(=C(C#N)C#N)C=C(C)O2)ccc1NCc1ccc(N)cc1]

16. The method of claim 1, wherein the compound of Formula I is

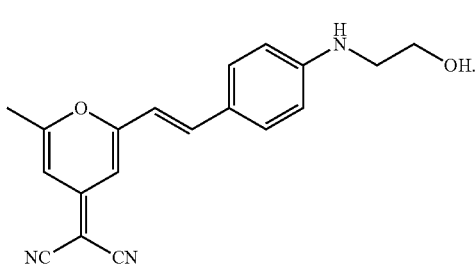 [SMILES: CC1=CC(=C(C#N)C#N)C=C(/C=C/c2ccc(NCCO)cc2)O1]

17. The method of claim 1, wherein the compound of Formula I is

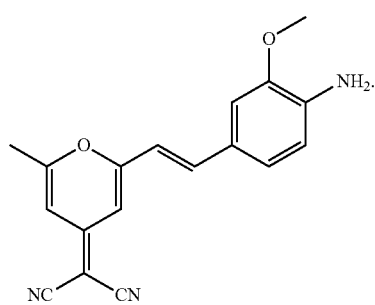

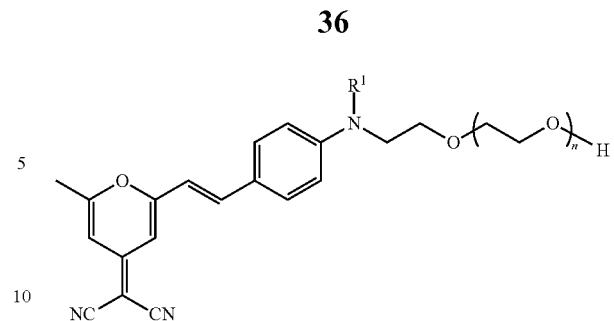

wherein $R^1$ is a hydrogen, a hydroxyl group, a $C_1$-$C_{30}$ aliphatic radical, a $C_3$-$C_{30}$ cycloaliphatic radical, or a $C_2$-$C_{30}$ aromatic radical; and n is an integer between 0 and 4.

18. The method of claim 1, wherein the compound of Formula I is

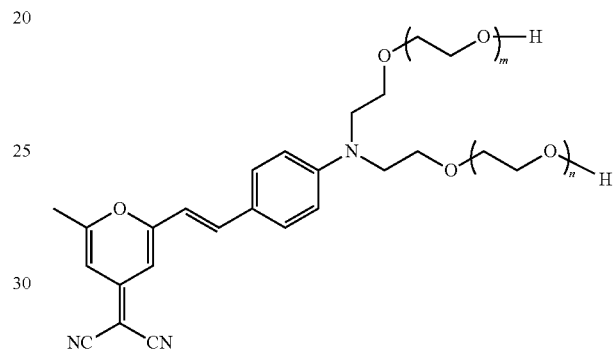

and wherein m and n are integers such that m+n is less than or equal to 4.

19. The method of claim 1, wherein the administering comprises intravenous injection, intraperitoneal injection, subcutaneous injection, intramuscular injection, intrathecal injection, intracerebral injection, intracerebroventricular injection, intraspinal injection, or combinations thereof.

20. The method of claim 1, wherein the detecting is effected by gamma imaging, fluorescence microscopy, laser-confocal microscopy, cross-polarization microscopy, autoradiography, magnetic resonance imaging, magnetic resonance spectroscopy, or combinations thereof.

21. The method of claim 1, wherein the detecting is effected by:

applying a light source on the subject, wherein the light source is tuned to the spectral excitation characteristics of the compound of Formula I; and observing the subject through an optical filter tuned to the spectral emission characteristics of the compound of Formula I.

22. The method of claim 1, wherein the quantifying step comprises measuring a radioactivity of the agent present in the subject and wherein the agent comprises the radioactive derivative of Formula I.

23. The method of claim 1, wherein the myelin-associated neuropathy comprises multiple sclerosis, Alzheimer's disease, Guillain-Barré syndrome, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy-induced neuropathy, or a combination thereof.

* * * * *

UNITED STATES PATENT AND TRADEMARK OFFICE
CERTIFICATE OF CORRECTION

PATENT NO. : 9,040,019 B2
APPLICATION NO. : 13/689819
DATED : May 26, 2015
INVENTOR(S) : Siclovan et al.

It is certified that error appears in the above-identified patent and that said Letters Patent is hereby corrected as shown below:

In the specification

In Column 1, Line 8, delete "R01-EB022872" and insert -- R01-EB011872 --, therefor.

In Column 2, Line 10, delete "bather" and insert -- barrier --, therefor.

In Column 11, Line 17, delete "R'," and insert -- $R^1$, --, therefor.

In Column 11, Line 32, delete "bather" and insert -- barrier --, therefor.

In Column 11, Line 33, delete "bather" and insert -- barrier --, therefor.

In Column 22, Line 24, delete "determined" and insert -- determined. --, therefor.

In Column 30, Line 32, delete "2-Hydroxypropyl-3-Cyclodextrin" and insert -- 2-Hydroxypropyl-β-Cyclodextrin --, therefor.

Signed and Sealed this
Fifth Day of July, 2016

Michelle K. Lee
*Director of the United States Patent and Trademark Office*